United States Patent [19]

Satow et al.

[11] Patent Number: 5,773,388

[45] Date of Patent: Jun. 30, 1998

[54] PYRIMIDINE DERIVATIVES, HERBICIDES AND PLANT GROWTH REGULATORS

[75] Inventors: Jun Satow; Yasuo Kondo; Yoshihiro Kudo; Takumi Mikashima, all of Funabashi; Tsutomu Nawamaki, Shiraoka-machi; Yoichi Ito, Shiraoka-machi; Kazuhisa Sudo, Shiraoka-machi; Kunimitsu Nakahira, Shiraoka-machi; Shigeomi Watanabe, Shiraoka-machi; Kimihiro Ishikawa, Shiraoka-machi, all of Japan

[73] Assignee: Nissan Chemical Industries, Ltd., Tokyo, Japan

[21] Appl. No.: 592,298

[22] PCT Filed: Aug. 9, 1994

[86] PCT No.: PCT/JP94/01311

§ 371 Date: Feb. 9, 1996

§ 102(e) Date: Feb. 9, 1996

[87] PCT Pub. No.: WO94/01311

PCT Pub. Date: Aug. 9, 1994

[30] Foreign Application Priority Data

Aug. 10, 1993 [JP] Japan .................................... 5-198328
Nov. 1, 1993 [JP] Japan .................................... 5-273392
Jul. 26, 1994 [JP] Japan .................................... 6-174575

[51] Int. Cl.⁶ .......................... C07D 239/26; A01N 43/54
[52] U.S. Cl. .......................... 504/239; 504/168; 504/177; 504/178; 544/242; 544/335

[58] Field of Search ..................................... 504/398, 239, 504/177, 178, 168; 544/242, 334, 335

[56] References Cited

FOREIGN PATENT DOCUMENTS 0 272 813  6/1988   European Pat. Off. .

OTHER PUBLICATIONS

Mosti et al, J. Het. Chem, vol. 20, pp. 649–654 (1983).
Gromov et al, Chemical Abstracts, vol. 119 entry 180724 (1993).
Mosti et al. Chemical Abstracts vol. 99, entry 194910 (1983).

*Primary Examiner*—John M. Ford
*Attorney, Agent, or Firm*—Oblon, Spivak, McClelland, Maier & Neustadt, P.C.

[57] ABSTRACT

Novel pyrimidine derivatives of the formula (I):

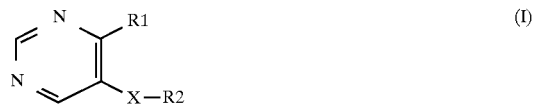

wherein R1 is a $C_1$–$C_6$ haloalkyl group, a $C_1$–$C_6$ alkyl group, a $C_3$–$C_6$ cycloalkyl group or the like, R2 is a hydrogen atom, a $C_1$–$C_6$ alkyl group, a $C_3$–$C_6$ cycloalkyl group or the like, and X is a carbonyl group or —C(R3)OH (wherein R3 is a hydrogen atom, a $C_1$–$C_6$ alkyl group or the like).

12 Claims, No Drawings

PYRIMIDINE DERIVATIVES, HERBICIDES AND PLANT GROWTH REGULATORS

This is a 371 of PCT/JP94/01311 filed Aug. 9, 1994.

TECHNICAL FIELD

The present invention relates to novel pyrimidine derivatives, and herbicides and plant growth regulators containing such derivatives as active ingredients. The derivatives are also useful as intermediates for medicines and agricultural chemicals.

BACKGROUND TECHNIQUE

It has not been known at all that the group of compounds of the present invention which contain a pyrimidine ring having hydrogen atoms at the 2- and 6-positions and having specific substituents introduced at the 4- and 6-positions exhibit a herbicidal activity and a plant growth regulating activity. Further, none of their chemical structures have not been known except that those of three compounds, 4-methyl-5-acetylpyrimidine, 4-tert-butyl-5-tert-butylcarbonylpyrimidine and 4-phenyl-5-benzoylpyrimidine, are disclosed in Journal of Heterocyclic Chemistry, Vol. 20, 1983, p. 649.

In order to protect important crop plants such as rice, soybean, wheat, corn, cotton and sugar beet and increase their productivities, many herbicides have been put in practical use so far. These herbicides are roughly classified into three categories, those for upland fields, for paddy fields, and for non-agricultural fields, according to the application site. Further, each category can be classified as a soil incorporation type, a pre-emergence soil treatment type and a post-emergence treatment (foliage treatment) type, according to the manner of application.

With the recent global population explosion, the productivities of important crop plants will undoubtedly affect the food economy of each country. These changes will be inevitably accompanied by changes of the conventional mode of agriculture toward the 21st century. Actually, development of herbicides which can economically and effectively kill or control weeds detrimental to the growth of crop plants, is becoming more and more important to farmers than ever.

As such herbicides, chemicals which meet the following requirements are desired to be developed.

Those having high herbicidal effects at low doses (it is necessary to kill weeds at as low doses as possible from the viewpoint of environmental protection), those having adequate residual activities (since a problem that soil-persistent chemicals damage next crops has arisen recently, it is important to show an adequate residual activity after application), those which promptly kill weeds upon application (it is possible to sow or transplant next crops soon after chemical treatment), those which do not require frequent treatment (it is important for farmers to minimize the frequency of cumbersome weed control operations), those intended to control a wide range of weeds (chemicals capable of controlling a variety of weeds having different properties such as broad-leaves weeds, graminaceous weeds and perennial weeds independently, are desirable), those which can be applied by various methods (a stronger herbicidal effect can be obtained by combining an effect of soil treatment, an effect of foliage treatment and so on), and those which do not show any problematic phytotoxicity against crop plants (in a field where a crop plant coexists with weeds, those capable of selectively killing weeds are desired), are preferred. However, no existing herbicides satisfy all of these requirements.

On the other hand, diseases and insect pests, which are a hindrance to farmers in crop cultivation, are effectively controlled by excellent fungicides and insecticides. However, in addition to these harmful organisms, there are other factors which lower the yield and the qualities. For example, wind or rain lodges barley, rye, wheat, rice, corn, soybean or cotton at time of harvesting. One of the easiest and most effective preventive measures is to suppress inter-node elongation for the purpose of preventing lodging of these crop plants, and therefore development of growth retardants which have no influence on yield is becoming more and more necessary than ever. As such growth retardants, chemicals which meet the following requirements are desired to be developed.

Those having high dwarfing effects at low doses (especially from the viewpoint of environmental protection, it is necessary to exhibit dwarfing effects at as low doses as possible), those having adequate residual effects (it is important that the residual amounts in soil after application are small), those which act moderately (a sudden action is not desirable), a chemical treatment is preferred to be conducted once, basically (it is important for farmers to reduce the frequency of cumbersome operations), those which can be applied by various methods (it is possible to select an appropriate application method for a crop, from soil treatment, foliage treatment, seed treatment and so on), it is preferred to inhibit foliage growth for the purpose of translocation of nutrients to flowers or fruits rather than to foliage (which leads to increase in the yield). Further, those having little growth retarding effects on roots are preferred.

On the other hand, there is a desire for uses in inhibiting the growth of lawn grasses, controlling fruit tree turions, dwarfing ornament plants for the purpose of high commercial values, suppressing the growth of hedge plants and controlling a flowering time. Since complete death of weeds in a non-agricultural field causes run-off of the soil, in recent years it is necessary to control weed length and avoid killing them.

DISCLOSURE OF THE INVENTION

The present inventors have conducted extensive researches on the herbicidal action and the plant growth regulating action of the novel pyrimidine derivatives under these circumstances. As a result, they found that pyrimidine derivatives of the following formula exhibit remarkable herbicidal activities and plant growth regulating activities. The present invention has been accomplished on the basis of this discovery. Namely, the present invention provides a novel pyrimidine derivative of the formula (I) (hereinafter referred to as the compound of the present invention):

[wherein R1 is a $C_1$–$C_6$ haloalkyl group, a $C_1$–$C_6$ alkyl group, a $C_3$–$C_6$ cycloalkyl group, a $C_3$–$C_6$ halocycloalkyl group or an optionally substituted phenyl group (wherein the substituent is selected from the group consisting of a halogen atoms, a $C_1$–$C_4$ alkyl group, a $C_1$–$C_4$ alkoxy group, a $C_1$–$C_3$ haloalkyl group, a $C_1$–$C_3$ haloalkoxy group and a phenyl group), R2 is a hydrogen atom, a $C_1$–$C_6$ alkyl group, a $C_3$–$C_6$ cycloalkyl group, a $C_3$–$C_6$ cycloalkyl($C_1$–$C_4$)alkyl group, a $C_1$–$C_6$ haloalkyl group, a $C_3$–$C_6$ halocycloalkyl group, a $C_3$-$C_8$ alkenyl group, a $C_3$-$C_8$ alkynyl group, a $C_1$-$C_2$ sulfonyl($C_1$-$C_4$)alkyl group, a $C_1$-$C_4$ alkylthio ($C_3$-$C_6$)cycloalkyl group and an optionally substituted phenyl group (wherein the substituent is selected from the group consisting of a halogen atom, a $C_1$-$C_4$ alkyl group, a $C_1$-$C_4$ alkoxy group, a $C_1$-$C_3$ haloalkyl group, a $C_1$-$C_3$ haloalkoxy group and a phenyl group), X is a carbonyl group or —C(R3)OH (wherein R3 is a hydrogen atom, a $C_1$-$C_6$ alkyl group, a $C_3$-$C_8$ alkenyl group, a $C_3$-$C_8$ alkynyl group or an optionally substituted phenyl group (wherein the substituent is selected from the group consisting of a halogen atom, a $C_1$-$C_4$ alkyl group, a $C_1$-$C_4$ alkoxy group, a $C_1$-$C_3$ haloalkyl group, a $C_1$-$C_3$ haloalkoxy group or a phenyl group) (provided that when the carbon atom is an optically active carbon atom, the lacemate and both of the two isolated optical isomers are included)]. The present invention also provides herbicides and plant growth regulators containing the compounds of the present invention.

Some of the compounds of the present invention exhibit high herbicidal activities as a herbicide for upland fields and non-agricultural fields, either in soil treatment or in foliage treatment at low doses against broad-leaved weeds such as Solanaceous weeds (Solanaceae) represented by black nightshade (*Solanum nigrum*) and jimsonweed (*Datura stramonium*), Malvaceous weeds (Malvaceae) represented by velvetleaf (*Abutilon theophrasti*) and prickly sida (*Sida spinosa*), Conolvulaceous weeds (Convolvulaceae) presented by morningglories (*Ipomoea spps.*) including common morningglory (*Ipomoea purpurea*) and bindweeds (*Calystegia spps.*), Amaranthaceous weeds (Amaranthaceae) represented by livid amaranth (*Amaranthus lividus*) and redroot pigweed (*Amaranthus retroflexus*), Composite weeds (Compositae) presented by common cocklebur (*Xanthium pensylvanicum*), common ragweed (*Ambrosia artemisiaefolia*), sunflower (*Helianthus annuus*), hairy galinsoga (*Galinsoga ciliata*), creeping thistle (*Cirsium arvense*), common groundsel (*Senecio vulgaris*) and annual fleabane (*Erigeron annus*), Cruciferous weeds (Cruciferae) represented by India field cress (*Rorippa indica*), kedlock (*Sinapis arvensis*) and shepherd's purse (*Capsella bursapastoris*), Polygonaceous weeds (Polygonaceae) represented by posumbu knotweed (*Polygonum blumei*) and wild buckwheat (*Polygonum convolvulus*), Portulacaceous weeds (Portulacaceae) represented by common purslane (*Portulaca oleracea*), Chenopodiaceous weeds (Chenopodiaceae) represented by common lambsquater (*Chenopodium album*), figleaved goosefoot (*Chenopodium ficifolium*) and kochia (*Kochia scoparia*), Caryophyllaceous weeds (Caryophyllaceae) represented by common chickweed (*Stellaria media*), Scrophulariaceous weeds (Scrophulariaceae) represented by persian speedwell (*Veronica persica*), Commelinaceous weeds (Commelinaceae) represented by asiatic dayflower (*Commelina communis*), Labiate weeds (Labiatae) represented by dead-nettle (*Lamium amplexicaule*) and red dead-nettle (*Lamium purpureum*), Euphorbiaceous weeds (Euphorbiaceae) represented by prostrate spurge (*Euphorbia supina*) and spotted spurge (*Euphorbia maculata*), Rubiaceous weeds (Rubiaceae) represented by bed straw (*Galium spurium*) and indian madder (*Rubia akane*), Violaceous weeds (Violaceae) presented by violet (*Viola mandshurica*), and Leguminous weeds (Leguminosae) represented by hempsesbania (*Sesbania exaltata*) and sicklepod (*Cassia obtusifolia*), and various cropland weeds such as Graminaceous weeds represented by shattercane (*Sorgham bicolor*), fall panicum (*Panicum dichotomiflorum*), johnsongrass (*Sorghum halepense*), barnyardgrass (*Echinochloa crus-galli* var. *crus-galli*), barnyardgrass (*Echinochloa crus-galli* var. *praticola*), barnyardgrass (crop) (*Echinochloa utilis*), large crabgrass (*Digitaria adscendens*), wild oat (*Avena fatua*), goosegrass (*Eleusine indica*), green foxtail (*Setaria viridis*) and water foxtail (*Alopecurus aegualis*), and Cyperaceous weeds represented by purple nutsedge (*Cyperus rotundus, Cyperus esculentus*).

Further, the compounds of the present invention exhibit high herbicidal activities as a herbicide for paddy fields either in submerged soil treatment or in foliage treatment at low doses against various paddy weeds such as Alismataceous weeds (Alismataceae) represented by narrow leaf waterplantain (*Alisma canaliculatum*), arrowhead (*Sagittaria trifolia*) and japanese ribbon wapato (*Sagittaria pygmaea*), Cyperaceous weeds (Cyperaceae) represented by smallflower umbrellaplant (*Cyperus difformis*), perennial flat sedge (*Cyperus serotinus*), bulrush (*Scirpus juncoides*) and water chestnut (*Eleocharis kuroquwai*), Scrophulariaceous weeds (Scrothulariaceae) represented by false pimpernel (*Lindemia pyxidaria*), Potenderiaceous weeds (Potenderiaceae) represented by ducksalad (*Monochoria vaginalis*), Potamogenaceous weeds (Potamogetonaceae) represented by roundleaf pondweed (*Potamogeton distinctus*), Lythraceous weeds (Lythraceae) represented by toothcup (*Rotala indica*), barnyardgrass (*Echinochloa oryzicola*), barnyardgrass (*Echinochloa crus-galli* var. *formosensis*) and barnyardgrass (*Echinochloa crus-galli* var. *crus-galli*).

Further, the compounds of the present invention are found to have a high level of safety for important crop plants such as rice, wheat, barley, sorgo, peanut, corn, soybean and cotton and sugar beet.

Some of the compounds of the present invention can be used as a plant growth regulator for upland fields, paddy fields or non-agricultural fields, in soil, foliage or seed treatment, to inhibit of growth or elongation of broad-leaved weeds such as black nightshade, jimsonweed, velvetleaf, prickly sida, common morningglory, livid amaranth, redroot pigweed, common cocklebur, common ragweed, sunflower, hairy galinsoga, creeping thistle, common groundsel, annual fleabane, India field cress, kedlock, shepherd's purse, posumbu knotweed, wild buckwheat, common purslane, common lambsquater, figleaved goosefoot, kochia, common chickweed, persian speedwell, asiatic dayflower, dead-nettle, red deadnettle, prostrate spurge, spotted spurge, bedstraw, indian madder, violet, hempsesbania, sicklepod and hairy beggarticks, graminaceous weeds such as shattercane, fall panicum, johnsongrass, barnyardgrass, blackgrass, large crabgrass, wild oat, goosegrass, green foxtail and water foxtail, cyperaceous weeds such as purple nutsedge, and various paddy weeds such as narrowleaf waterplantain, arrowhead, japanese ribbon wapato, smallflower umbrellaplant, perennial flat sedge, bulrush, water chestnut, false pimpernel, ducksalad, roundleaf pondweed, toothcup, barnyardgrass, and inhibit growth of these weeds without complete death of plants, which may cause soil erosion.

The compounds of the present invention can be used to prevent lodging, inhibit the elongation, strengthen stems, thicken stems, prevent spindly growth, shorten stems and shorten internose of crop plants such as rice, wheat, barley, rye, corn, soybeans, peanut, cotton, sunflower, sugar beet, potato, rape and sugar cane, and consequently they are expected to lead to increased crop yields and improved resistance to bad environments and diseases and insect pests. Further the compounds of the present invention can be used to inhibit lawn grass growth, and are useful for dwarfing ornamental plants, indoor plants, garden plants or greenhouse plants.

The compounds of the present invention can be used to inhibit a woody plant from growing or bearing flowers. For example, they are used for keeping a hedge in shape, controlling the shape of a fruit tree (for example, apple, pear, cherry, peach, grapevine and western pear), or making pruning less necessary. Further, the compounds of the present invention can be used for flowering time control, branching control or stimulation of axillary bud growth through destruction of apical dominance.

Recently, a social problem of hay fever that pollens of cedar and Japanese cypress pollens induce city people's allergy has emerged. Use of the compounds of the present invention make it possible to inhibit and control flower bud formation and flower bearing of cedar and Japanese cypress which are responsible for hay fever. Pre-emergence seed treatment at a low dose may stimulate germination. In this case, they exert an initial growth stimulation action without inhibiting germination or elongation.

Therefore, the compounds of the present invention can be used as an active ingredient of herbicides and plant growth regulators for upland fields, paddy fields, lawns, orchards, pastures and other non-agricultural fields. Now, various methods for producing them will be described in details.

The compounds of the present invention can be synthesized by the methods represented by the following Scheme 1 to 3 (in Scheme 1 to 3, R1 to R3 are as defined above, each of Ra and Rb is a $C_1$–$C_3$ alkyl group, Met is a metal atom such as Mg or Zn, and Hal is a halogen atom).

The starting material, 2,4-dicarbonyl compound (II), can be easily synthesized in accordance with the methods disclosed in The Chemistry of the Carbonyl Group, p. 273, written by D. P. N. Satchell and R. S. Satchell, edited by Saul Patai (published by Wiley-interscience, 1966) and Organic Reactions Vol. 1, p. 266, written by C. R. Hauser and B. E. Hudson, Jr. (published by John Wiley & Sons, Inc., 1942).

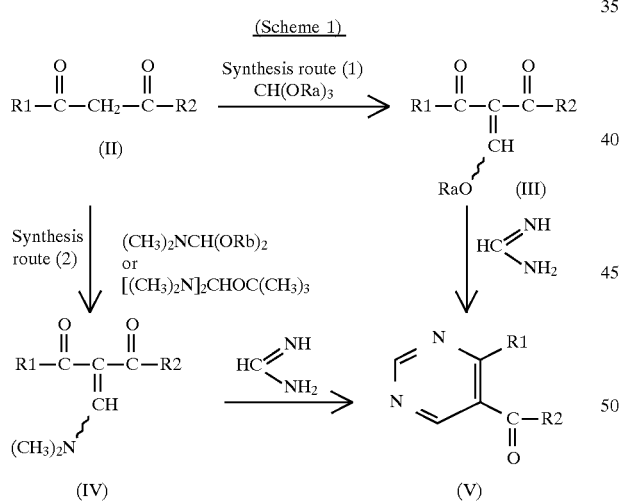

(1) Synthesis route (1) in Scheme 1 indicates a method of producing a pyrimidine derivatives (V) of the present invention (wherein X: C=O), which comprises reacting a 2,4-dicarbonyl compound (II) with an orthoformic ester derivative and then reacting the resulting 3-alkoxy methylene-2,4-dicarbonyl derivative (III) with a formamidine.

(2) Synthesis route (2) in Scheme 1 indicates a method of producing a pyrimidine derivative (V) of the present invention (wherein X: C=O), which comprises reacting a 2,4-dicarbonyl compound (II) with an N,N-dimethylformamide dialkylacetal or tert-butoxy-bis(dimethylamino)methane and then reacting the resulting 3-dimethylaminomethylene-2,4-dicarbonyl derivative (IV) with a formamidine.

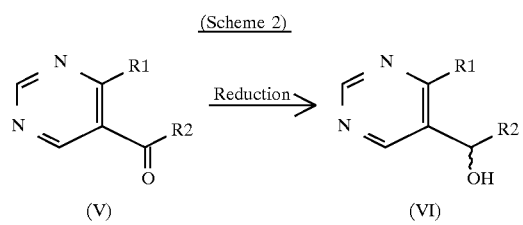

(3) Scheme 2 indicates a method wherein a pyrimidine derivative (V) (wherein X: C=O) is converted into a corresponding alcohol (VI) (X: CH—OH) by a suitable reduction method (for example, $NaBH_4$ or $BH_3$) or asymmetric reduction.

When the resulting alcohol (VI) is racemic, each of the optically active alcohols can be obtained through a suitable optical resolution, if necessary.

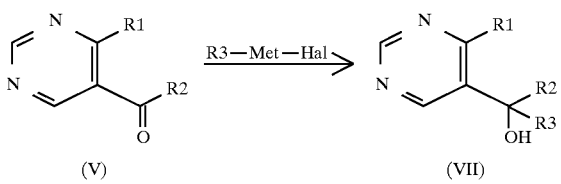

(4) Scheme 3 indicates a method of producing a compound (VII), which comprises reacting a pyrimidine derivative (V) with R3-Met-Hal (provided that the case that R3 is a hydrogen atom is excluded).

Now, the syntheses of the compounds of the present invention and their intermediates will be described in detail with reference to Examples. However, it should be understood that the present invention is by no means restricted by such specific Examples.

BEST MODE OF AN EMBODIMENT OF THE PRESENT INVENTION

EXAMPLE 1

Synthesis of 1-Choro-1,1-difluoro-3-ethoxymethylene-2,4-pentanedione (Compound No. 203)

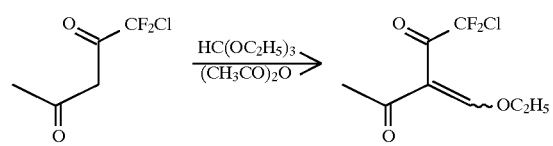

A mixed solution containing 50 g of 1-chloro-1,1-difluoro-2,4-pentanedione, 60 g of ethyl orthoformate and 82 g of acetic anhydride was refluxed with stirring for 2 hours. After a Dean-Stark apparatus (water separator) was fixed, the solution was refluxed for additional 4 hours, while about 100 ml of water was removed. After it was allowed to cool, vacuum distillation was conducted to obtain 32.2 g of the desired product as a pale red liquid. Boiling point 95°–118° C./1.6 mmHg.

EXAMPLE 2

Synthesis of 5-Acetyl-4-chlorodifluoromethylpyrimidine (Compound No. 1)

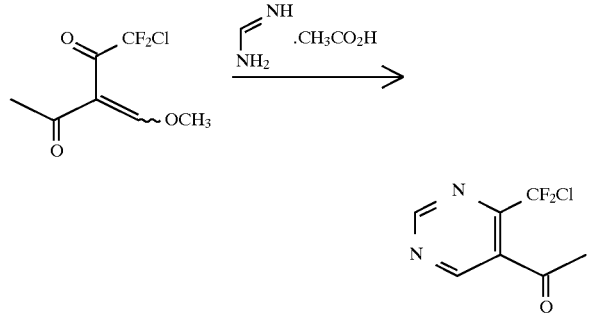

To 50 ml of dry ethanol, 0.9 g of metal sodium was added under cooling with ice to prepare sodium ethoxide. To this solution, 8.4 g of formamidine acetate which had been fully dried by means of a vacuum pump was added with stirring. Then, a solution of 8 g of 1-chloro-1,1-difluoro-3-ethoxymethylene-2,4-pentanedione dissolved in 20 ml of ethanol was added dropwise under cooling with ice. After the dropwise addition, the reaction solution was warmed to room temperature, and heated and refluxed with heating for 1.5 hours. The reaction solution was allowed to cool and after addition of water, ether extraction was carried out. The ether layer was dried over anhydrous sodium sulfate, and the solvent was distilled off under reduced pressure. The residue was subjected to vacuum distillation, and after purification by column chromatography (developing solvent: $CHCl_3$), 2.5 g of the desired product was obtained. Boiling point 65°–70° C./1.3 mmHg, $n_D^{20.7}$ 1.4787

EXAMPLE 3

Synthesis of 4-Chlorodifluoromethyl-5-(1-hydroxyethyl)pyrimidine (Compound No. 101)

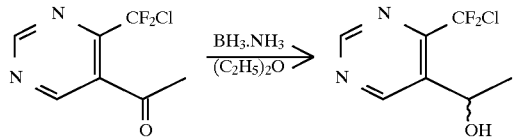

0.4 g of 5-acetyl-4-chlorodifluoromethylpyrimidine was dissolved in 10 ml of dry diethyl ether, then, an excess of a borane ammonia complex was added under cooling with ice, and the mixture was stirred overnight at room temperature. After addition of water, extraction with diethyl ether was carried out. The ether layer was dried over anhydrous sodium sulfate, and the solvent was distilled off under reduced pressure to obtain 0.32 g of the desired product as a viscous liquid. $n_D^{19.9}$ 1.4899

EXAMPLE 4

Synthesis of 5-(1-Hydroxyethyl)-4-trifluoromethylpyrimidine (Compound No. 102)

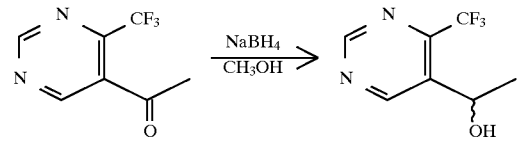

0.5 g of 5-acetyl-4-trifluoromethylpyrimidine was dissolved in 10 ml of dry methanol. 0.03 g of sodium boron hydride was added, and the mixture was stirred for 30 minutes under cooling with ice, and then further stirred overnight at room temperature. After the completion of the reaction, the solvent was distilled off, and 40 ml of a 1:1 solvent mixture of chloroform/water was added for chloroform extraction. After the chloroform layer was dried over anhydrous sodium sulfate, the solvent was distilled off under reduced pressure. After purification by column chromatography, 0.2 g of the desired product was obtained as a viscous liquid. $n_D^{19.9}$ 1.4549

EXAMPLE 5

Synthesis of 1-Chloro-1,1-difluoro-5,5-dimethyl-2,4-hexanedione (Compound No. 301)

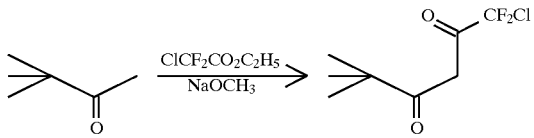

7.1 g of sodium methoxide was added to 100 ml of dry ether, and the mixture was stirred. A solution of 20 g of ethyl chlorodifluoroacetate diluted with 25 ml of dry ether was added dropwise at room temperature. Further, a solution of 12.5 g of pinacolone diluted with 25 ml of dry ether was added dropwise, and the mixture was stirred overnight at room temperature. Then, to the reaction solution, a solution of 8.4 g of glacial acetic acid diluted with 100 ml of water and a solution of 23.6 g of copper (II) acetate dissolved in a proper amount of water were added dropwise successively. The dropwise addition was followed by stirring for about 10 minutes. Then, the ether was distilled off under reduced pressure and the solid mass was filtered off. After vacuum drying, 100 ml of 6N hydrochloric acid was added, and extraction with ethyl acetate was carried out. The ethyl acetate layer was dried over anhydrous sodium sulfate, and the solvent was distilled off under reduced pressure. Then, the residue was subjected to vacuum distillation to obtain 13 g of the desired product. (b.p. 54°–57° C./5 mmHg)

$^1$H-NMR δ(ppm) [solvent]; 1.24 (s, 9H, C(C$\underline{H}_3$)$_3$) 5.95 (s, 1H, enol olefin) 14.00 (br s, 1H, enol O$\underline{H}$), [CDCl$_3$], $^{13}$C-NMR δ(ppm) [solvent]; 27.2 (s, C($\underline{C}$H$_3$)$_3$) 39.3 (s, $\underline{C}$(CH$_3$)$_3$) 90.0 (t, $J_{F,C}$=2 Hz, ClCF$_2$C=$\underline{C}$) 120.3 (t, $J_{F,C}$=299 Hz, $\underline{C}$F$_2$Cl) 180.3 (t, $J_{F,C}$=30 Hz, ClCF$_2$$\underline{C}$=C) 202.2 (s, $\underline{C}$OC(CH$_3$)$_3$) [CDCl$_3$], $^{19}$F-NMR δ(ppm) [solvent]; 13.3 (s, 2F, ClCF$_2$) (ref. CF$_3$CO$_2$H) [CDCl$_3$].

EXAMPLE 6

Synthesis of 1-Chloro-1,1-difluoro-5,5-dimethyl-3-ethoxymethylene-2,4-hexanedione (Compound No. 204)

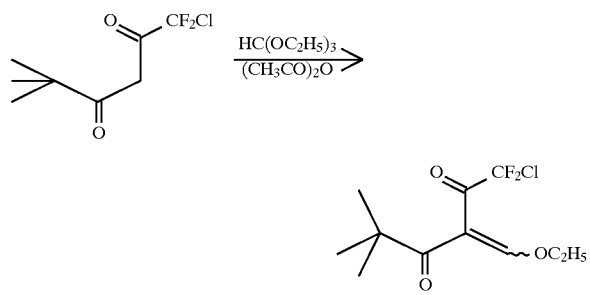

12.4 g of 1-chloro-1,1-difluoro-5,5-dimethyl-2,4-hexanedione and 12.4 g of ethyl orthoformate were added to 50 ml of acetic anhydride, and the mixture was refluxed under heating for 2 hours. After the solvent was distilled off under reduced pressure, the residue was subjected to vacuum distillation to obtain 6.8 g of the desired product. (b.p. 105°–107° C./2 mmHg)

EXAMPLE 7

Synthesis of 4-Chlorodifluoromethyl-5-pivaloylpyrimidine (Compound No. 3)

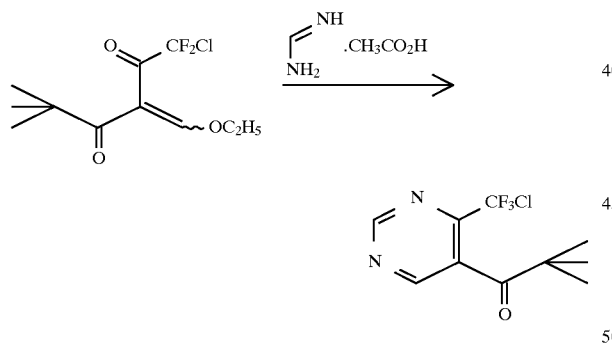

0.7 g of sodium methoxide and 1.25 g of formamidine acetate were added to 30 ml of dry methanol, and the mixture was stirred at room temperature for 30 minutes. A solution of 3 g of 1-chloro-1,1-difluoro-5,5-dimethyl-3-ethoxymethylene-2,4-hexanedione diluted with 5 ml of dry methanol was added dropwise, and after the addition, the mixture was refluxed under heating for 2 hours. The solvent was distilled off under reduced pressure, and after addition of water, extraction with ethyl acetate was carried out. The ethyl acetate layer was dried over anhydrous sodium sulfate, and the solvent was distilled off under reduced pressure. The residue was purified by thin-layer chromatography (developing solvent: hexane 80%, ethyl acetate 20%) to obtain 0.6 g of the desired product. $n_D^{20.0}$ 1.4675

EXAMPLE 8

Synthesis of 4-Chlorodifluoromethyl-5-(2,2-dimethyl-1-hydroxypropyl)pyrimidine (Compound No. 103)

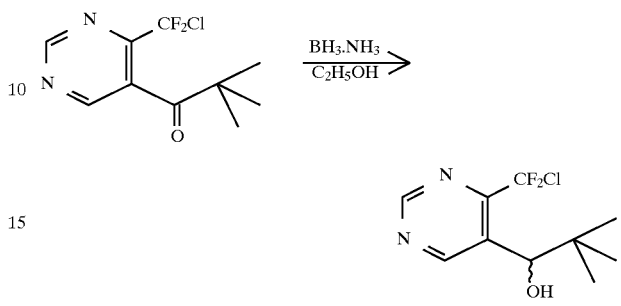

1.5 g of 4-chlorodifluoromethyl-5-pivaloylpyrimidine was dissolved in 50 ml of ethanol, then 1 g of a boron ammonia complex was added, and the mixture was stirred at room temperature for 1 hour. After the solvent was distilled off under reduced pressure, water was added, and extraction with chloroform was carried out. The extract layer was washed with water and then dried over anhydrous sodium sulfate. The solvent was distilled off under reduced pressure, and the residue was purified by thin-layer chromatography (developing solvent: chloroform/ethyl acetate=7/3) to obtain 1.1 g of the desired product as a viscous liquid. $n_D^{19.8}$ 1.4623

EXAMPLE 9

Synthesis of 1-(4-Chlorophenyl)-4,4-dimethylpentane-1,3-dione (Compound No. 303)

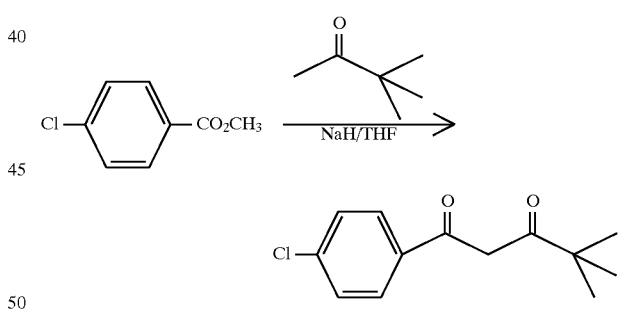

30 g of methyl 4-chlorobenzoate was dissolved in anhydrous THF, and 16.9 g of 60% sodium hydride was added under cooling with ice. 21.1 g of pinacolone was added dropwise, and the mixture was stirred under heating at 50° C. for 6 hours. Then, 100 ml of water was added dropwise under cooling with ice, and the solvent was distilled off under reduced pressure. 200 ml of water and 100 ml of 6N hydrochloric acid were added thereto, and then extraction with ethyl acetate was carried out. The extract layer was dried over anhydrous sodium sulfate, and the solvent was distilled off under reduced pressure. The residue was purified by silica gel column chromatography (developing solvent: chloroform/hexane=2/8) to obtain 43 g of the desired product as a viscous liquid. $n_D^{20.0}$ 1.5012

EXAMPLE 10

Synthesis of 1-(4-Chlorophenyl)-4,4-dimethyl-2-(N,N-dimethylaminomethylene)-1,3-pentanedione (Compound No. 206)

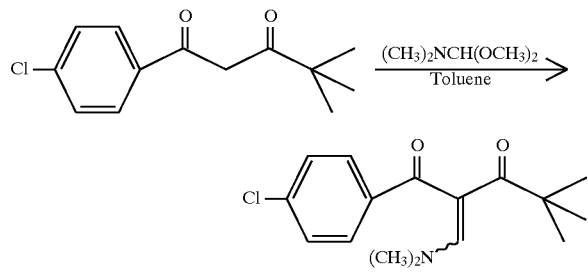

17 g of 1-(4-chlorophenyl)-4,4-dimethyl-1,3-pentanedione and 18 g of dimethylformamide dimethylacetal were added to 200 ml of dry toluene, and the mixture was refluxed under heating for 2 hours, and then the methanol was distilled off over 1 hour. The solvent was distilled off, and the residue was purified by silica gel chromatography (developing solvent: chloroform/hexane=6/4) to obtain 13.7 g of the desired product as a pale yellow solid.

m.p. 102°–104° C.

EXAMPLE 11

Syntheses of 4-(4-Chlorophenyl)-5-pivaloylpyrimidine and 4-t-Butyl-5-(4-chlorobenzoyl)pyrimidine (Compounds Nos. 5 and 6)

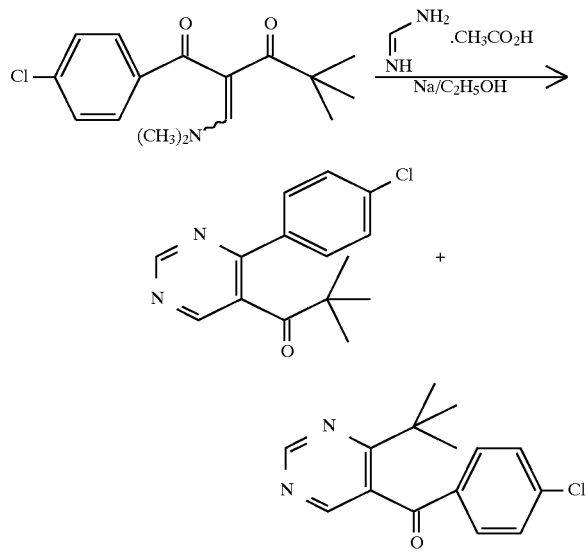

1 g of metal sodium and 3.3 g of formamidine acetate were added to 150 ml of absolute ethanol, and the mixture was stirred at room temperature for 15 minutes. 8.5 of 1-(4-chlorophenyl)-4,4-diemthyl-2-(N,N-dimethylaminomethylene)-1,3-pentanedione was added thereto, and the mixture was refluxed under heating for 3 hours. 20 cc of water was added at room temperature, and then the solvent was distilled off under reduced pressure. After further addition of water, extraction with ethyl acetate was conducted. The extract layer was washed with water and dried over anhydrous sodium sulfate. The solvent was distilled off under reduced pressure, and the residue was separated by silica gel column chromatography (developing solvent; ethyl acetate/hexane=3/7) to obtain 4-t-butyl-5-(4-chlorobenzoyl)pyrimidine (yield: 2.5g, m.p.:75°–77° C.) and 4-(4-chlorophenyl)-5-pivaloylpyrimidine (yield 2.4 g, $n_D^{20.1}$ 1.5784).

EXAMPLE 12

Synthesis of 4-(4-Chlorophenyl)-5-(2,2-dimethyl-1-hydroxypropyl)pyrimidine (Compound No. 104)

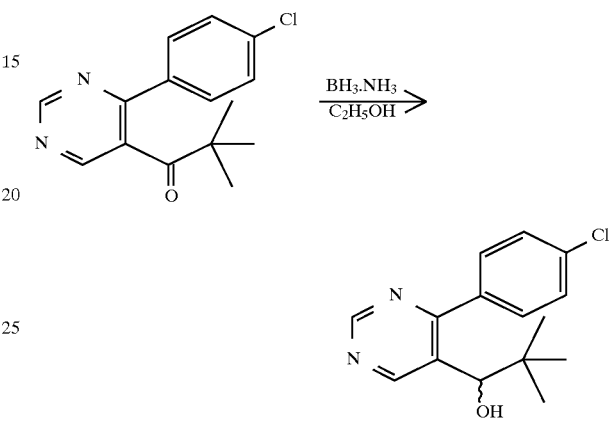

1.2 g of 4-(4-chlorophenyl)-5-pivaloylpyrimidine was dissolved in 20 ml of ethanol, then 1.2 g of a borane ammonia complex was added, and the mixture was stirred at room temperature for 30 minutes. After the solvent was distilled off under reduced pressure, water was added, and extraction with chloroform was carried out. The extract layer was washed with water and dried over anhydrous sodium sulfate. The solvent was distilled off to obtain 0.8 g of the desired product as a viscous liquid. $n_D^{20.2}$ 1.5575

EXAMPLE 13

Synthesis of 4-t-Butyl-5-[(4-chlorophenyl)hydroxymethyl]pyrimidine (Compound No. 105)

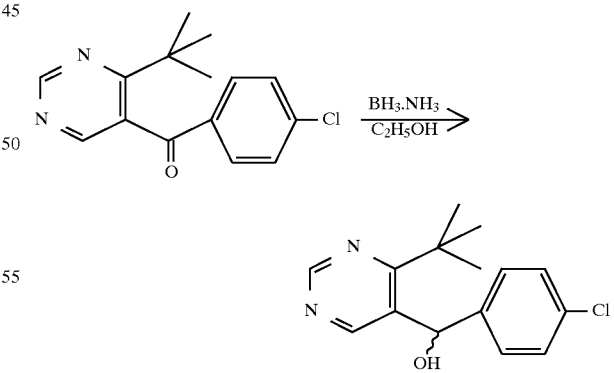

1 g of 4-t-butyl-5-(4-chlorobenzoyl)pyrimidine was dissolved in 20 ml of ethanol, and 0.8 g of a borane ammonia complex was added. The mixture was heated at 50° C.–60° C. for 1 hour, and further refluxed under heating for 30 minutes. After the solvent was distilled off under reduced pressure, water was added, and extraction with chloroform was carried out. The extract layer was washed with water and dried over anhydrous sodium sulfate. The solvent was distilled off under reduced pressure to obtain 0.6 g of the desired product as a viscous liquid. $n_D^{20.2}$ 1.5474

EXAMPLE 14

Synthesis of 1-Chloro-4-(4-chlorophenyl)-1,1-difluoro-2,4-butanedione (Compound No. 318)

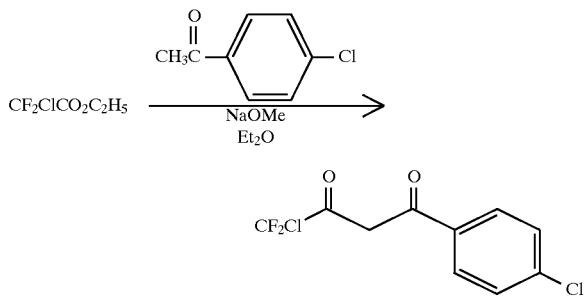

38 g of ethyl chlorodifluoroacetate was added to 22.7 g of sodium methoxide and 300 ml of dry ether under cooling with ice. 31 g of p-chloroacetophenone was gradually added thereto under cooling with ice. The mixture was stirred at room temperature for 12 hours. The solvent was distilled off. 150 ml of 6N hydrochloric acid was added under cooling with ice, and extraction with ethyl acetate was carried out. The extract layer was washed with water, and the solvent was distilled off. The resulting crude product was purified by silica gel column chromatography (developing solvent: chloroform), and thereby 49.5 g of the desired product was obtained as a pale yellow viscous liquid. m.p. 50°–51° C.

EXAMPLE 15

Synthesis of 1-Chloro-4-(4-chlorophenyl)-1,1-difluoro-3-ethoxymethylene-2,4-butanedione

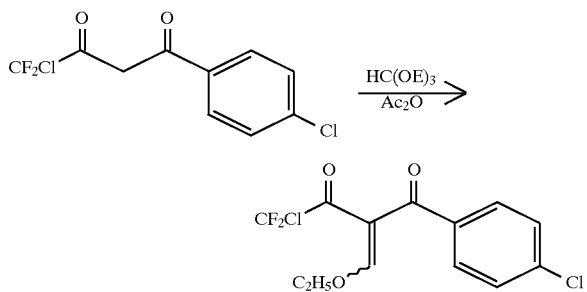

A mixture of 49.5 g of 1-choro-4-(4-chlorophenyl)-1,1-difluoro-2,4-butanedione, 41.3 g of ethyl orthoformate and 57 g of acetic anhydride was refluxed under heating for 4 days. The solvent was distilled off to obtain 60.4 g of the crude product, which was used for the next reaction directly.

EXAMPLE 16

Synthesis of 5-(4-Chlorobenzoyl)-4-chlordifluoromethylpyrimidine (Compound No. 20)

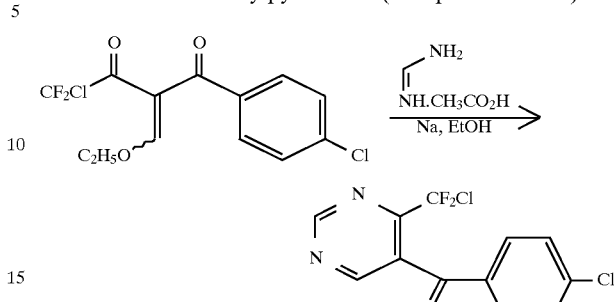

6 g of metal sodium and 500 ml of dry ethanol was mixed to prepare a sodium ethoxide solution. 23.3 g of formamidine acetate was added to the solution, and the mixture was stirred at room temperature for 15 minutes. 60.4 g of 1-chloro-4-(4-chlorophenyl)-1,1-difluoro-3-ethoxymethylene-2,4-butanedione (crude product) was gradually added under cooling with ice. The mixture was refluxed under heating for 2 hours. The solvent was distilled off under reduced pressure. 300 ml of ice water was added, and then extraction with ethyl acetate was carried out. The extract layer was washed with water, and the solvent was distilled off under reduced pressure.

The resulting crude product was purified by silica gel column chromatography (developing solvent: chloroform/hexane=1/1) to obtain 27 g of the desired product as a pale yellow liquid. $n_D^{20.8}$ 1.5742

EXAMPLE 17

Synthesis of 4-Chlorodifluoromethyl-5-[(4-chlorophenyl)hydroxymethyl]pyrimidine (Compound No. 119)

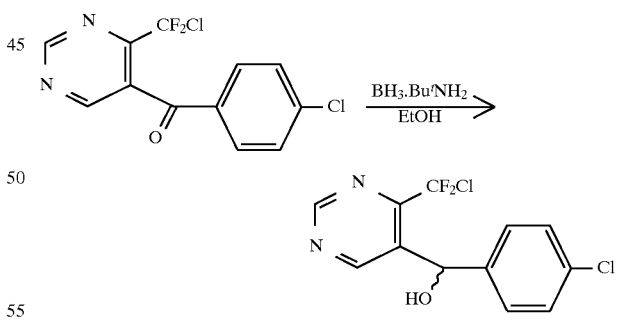

12 g of 5-(4-chlorobenzoyl)-4-chlorodifluoromethylpyrimidine and 6 g of a t-butylamine borane complex were added to 100 ml of ethanol, and the resulting mixture was stirred at 0° C. for 2 hours. Then, 20 ml of acetone was added thereto, and the mixture was stirred at 0° C. for 1 hour. The solvent was distilled off under reduced pressure, and the residue was purified by silica gel column chromatography (developing solvent: chloroform) to obtain 11.1 g of the desired product as a pale yellow viscous liquid. $n_D^{20.3}$ 1.5563

EXAMPLE 18

Synthesis of 1-Chloro-4-cyclohexyl-1,1-difluoro-2,4-butanedione (Compound No. 305)

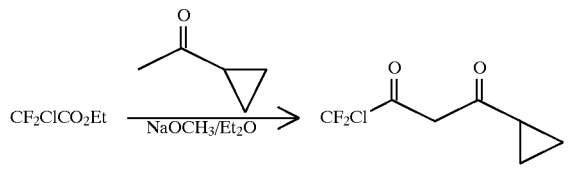

74.8 g of sodium methoxide was added to 1 l of ether, and a solution of 200 g of ethyl chlorodifluoroacetate in 300 ml of ether was added dropwise thereto under stirring at 0° C. Then, a solution of 106 g of cyclopropyl methyl ketone in 300 ml of ether was gradually added to the reaction solution, and after the addition, the mixture was stirred at room temperature for 8 hours. The solvent was distilled off under reduced pressure, 300 ml of 6N hydrochloric acid was added to the residue, and extraction with ethyl acetate was carried out. The extract layer was washed with water, and the solvent was distilled off under reduced pressure to obtain 235.9 g of the desired product as a pale yellow liquid. $n_D^{20.6} 1.4788$

EXAMPLE 19

Synthesis of 1-Chloro-4-cyclohexyl-3-ethoxymethylene-1,1-difluoro-2,4-butanedione (Compound No. 207)

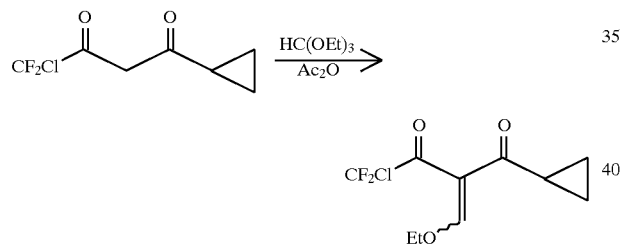

A mixture of 235.9 g of 1-chloro-4-cyclohexyl-1,1-difluoro-2,4-butanedione, 266.4 g of ethyl orthoformate and 367.2 g of acetic anhydride was refluxed under heating for 12 hours. The solvent was distilled off under reduced pressure to obtain 280.3 g of the desired product (crude product), which was directly used for the next reaction. A part of the crude product was further purified for measurement of the refractive index. $n_D^{20.6} 1.4787$

EXAMPLE 20

Synthesis of 4-Chlorodifluoromethyl-5-cyclopropylcarbonylpyrimidine (Compound No. 7)

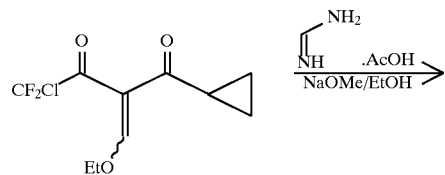

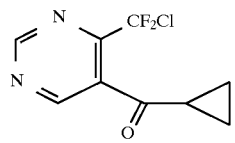

71.9 of sodium methoxide was added to 1 l of ethanol, and then 121.2 g of formamidine acetate was added. To the resulting mixture, 280 g of 1-chloro-4-cyclohexyl-3-ethoxymethylene-1,1-difluoro-2,4-butanedione was gradually added dropwise under cooling with ice. The mixture was refluxed under heating for an hour, and the solvent was distilled off under reduced pressure. 500 ml of water was added to the residue, and extraction with ethyl acetate was carried out. The solvent in the extract layer was distilled off under reduced pressure, and the residue was purified by silica gel column chromatography (developing solvent: chloroform/hexane=1/1) to obtain 101 g of the desired product. $n_D^{20.5} 1.4998$

EXAMPLE 21

Synthesis of 4-Chlorodifluoromethyl-5-(1-hydroxycyclopropylmethyl)pyrimidine (Compound No. 106)

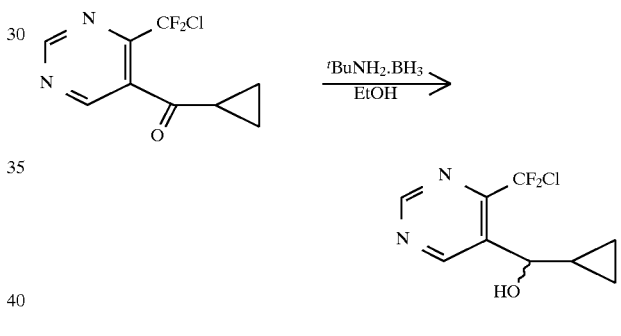

70 g of 4-chlorodifluoromethyl-5-cyclopropylcarbonylpyrimidine was added to 100 ml of ethanol, then, 15 g of a t-butylamine borane complex was further added under cooling with ice, and the mixture was stirred at room temperature for 2 hours. After addition of 30 ml of acetone, the mixture was stirred at room temperature for 1 hour, and the solvent was distilled off under reduced pressure. 100 ml of water was added to the residue, and extraction with ethyl acetate was carried out. The extract layer was washed with water, and the solvent was distilled off under reduced pressure. The residue was dried in vacuum to obtain 45 g of the desired product. $n_D^{20.5} 1.5020$

EXAMPLE 22

Synthesis of 4-Chlorodifluoromethyl-5-bromoacetylpyrimidine (Compound No. 11)

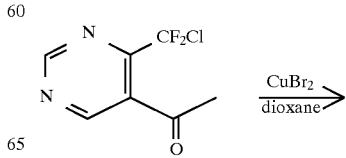

-continued

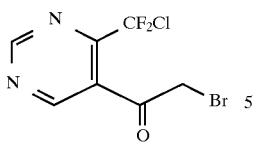

A mixture of 2.0 g of 5-acetyl-4-chlorodifluoromethylpyrimidine, 4.3 g of cupric bromide (CuBr$_2$) and 20 ml of dry dioxane was stirred at room temperature for a day, and then stirred under reflux for another day. Then, the insolubles were filtrated off and washed with a small amount of chloroform, and the filtrate thus obtained was distilled under reduced pressure. The resulting crude product was purified by preparative thin-layer chromatography (developing solvent: chloroform) to obtain 640 mg of the desired product as a pale yellow liquid.

EXAMPLE 23

Synthesis of 4-Chlorodifluoromethyl-5-(1-hydroxy-1-methylethyl)pyrimidine (Compound No. 110)

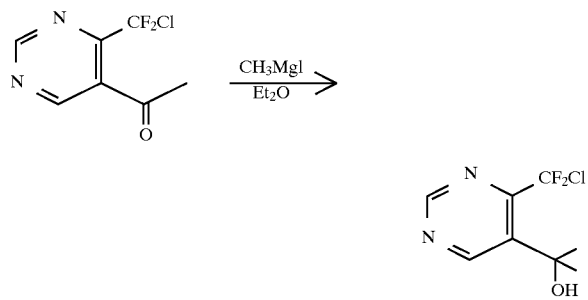

To a mixture of 470 mg of magnesium and 5 ml of dry ethyl ether, a solution of 2.76 g of methyl iodide dissolved in 15 ml of dry ethyl ether was added dropwise while the reaction mixture was kept under control so as to be refluxed moderately. After the dropwise addition, it was further refluxed for 45 minutes. The reaction mixture was allowed to cool to room temperature, then, 2 g of 5-acetyl-4-chlorodifluoromethylpyrimidine was quickly added dropwise thereto, and the reaction mixture was refluxed for another 1 hour. The reaction mixture was cooled with ice, and stirred while a saturated aqueous solution of ammonium chloride was added thereto. The ether layer was separated by decantation and washed with saturated aqueous salt solution three times in a separatory funnel. The organic layer was dried over anhydrous sodium sulfate, and the solvent was distilled off. The resulting crude product was subjected to preparatory thin-layer chromatography (developing solvent: chloroform) three times, and as a result, 131 mg of the desired product was obtained as a viscous liquid. $n_D^{20.6}$ 1.4982

EXAMPLE 24

Synthesis of 4-tert-Butyl-5-[(2-methylphenyl)hydroxymethyl]pyrimidine (Compound No. 117)

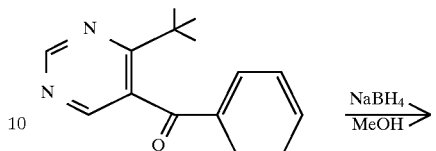

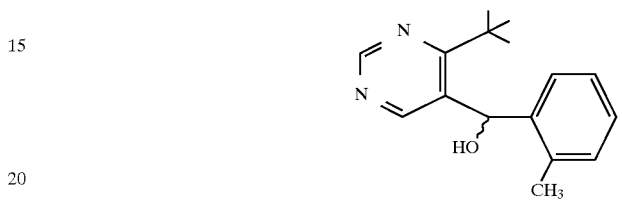

500 ml of sodium boron hydride (purity 92%) was added to a mixture of 1 g of 4-tert-butyl-5-(2-methylbenzoyl)pyrimidine and 20 ml of dry methanol, under cooling with ice, and the resulting mixture was stirred for 2 hours. The solvent was distilled off under reduced pressure, and to the resulting mixture, ice water and ethyl acetate were added, and the pH was adjusted to a level from 1 to 2 with concentrated hydrochloric acid with stirring. The organic layer was washed with saturated aqueous salt solution twice, and then dried over anhydrous sodium sulfate. The solvent was distilled off under reduced pressure to obtain 600 mg of the desired product as white crystals.

m.p. 125°–127° C.

The structures, the spectral data and the physical properties of the compounds of the present invention synthesized in the same manner as the above examples, including the compounds synthesized in the preceding Examples, are shown Tables 1-1, 1-2, 2-1 and 2-2. The structures and the physical properties of their intermediates are shown Tables 3-1 and 3-2.

TABLE 1-1

| Comp. No. | R1 | R2 |
|---|---|---|
| 1 | CF$_2$Cl | Me |
| 2 | CF$_3$ | Me |
| 3 | CF$_2$Cl | Bu$^{tert}$ |
| 4 | CF$_2$CF$_3$ | Me |
| 5 | 4-Cl-Phenyl | Bu$^{tert}$ |
| 6 | Bu$^{tert}$ | 4-Cl-Phenyl |
| 7 | CF$_2$Cl | Pr$^{cyclo}$ |
| 8 | 2,4-Cl$_2$-Phenyl | Bu$^{tert}$ |
| 9 | Bu$^{tert}$ | 2,4-Cl$_2$-Phenyl |
| 10 | CF$_2$Cl | Et |
| 11 | CF$_2$Cl | CH$_2$Br |
| 12 | 4-Cl-Phenyl | Pr$^{cyclo}$ |
| 13 | CF$_2$Cl | Pr$^n$ |

TABLE 1-1-continued

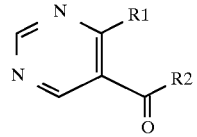

| Comp. No. | R1 | R2 |
|---|---|---|
| 14 | $CF_2Cl$ | $Pr^{iso}$ |
| 15 | $Bu^{tert}$ | 4-MeO-Phenyl |
| 16 | $Bu^{tert}$ | 2-MeO-Phenyl |
| 17 | $CF_2CF_2Cl$ | Me |
| 18 | $Bu^{tert}$ | 3-Me-Phenyl |
| 19 | $Bu^{tert}$ | 2-Me-Phenyl |
| 20 | $CF_2Cl$ | 4-Cl-Phenyl |
| 21 | $CF_2Cl$ | $2,4-Cl_2$-Phenyl |
| 22 | $CF_2Br$ | Me |
| 23 | $CF_2Cl$ | Phenyl |
| 24 | $CF_2Cl$ | 4-F-Phenyl |
| 25 | $CF_2Cl$ | 2-F-Phenyl |
| 26 | $CF_2Cl$ | 3-F-Phenyl |
| 27 | $CF_2Cl$ | 2-Cl-Phenyl |
| 28 | $CF_2Cl$ | 3-Cl-Phenyl |
| 29 | $CF_2Cl$ | $3,4-Cl_2$-Phenyl |
| 30 | CHFCl | $Pr^n$ |
| 31 | $CF_2H$ | $Pr^n$ |
| 32 | $CF_2Cl$ | 2-Me-Phenyl |

TABLE 1-2

| Comp. No. | Spectral data | Physical Properties |
|---|---|---|
| 1 | $^1$H-NMR δ (ppm) [solvent]:<br>2.65(t, J=1Hz, 3H, COCH$_3$),<br>8.90(s, 1H),<br>9.42(s, 1H),<br>[CDCl$_3$]<br>$^{13}$C-NMR δ (ppm) [solvent]:<br>31.35 (t, J$_{F,C}$=2.7Hz, COCH$_3$)<br>122.99(t, J$_{F,C}$=291Hz, CF$_2$Cl),<br>131.26(s, pyrimidine ring, 5-position),<br>155.07(t, J$_{F,C}$=31Hz, pyrimiding ring, 4-position),<br>156.91(s, pyrimidine ring, 6-position),<br>159.20(s, pyrimidine ring, 2-position),<br>197.69(s, C=O),<br>[CDCl$_3$]<br>$^{19}$F-NMR δ (ppm) [solvent]:<br>24.0(s, 2F, ClCF$_2$),<br>(ref. CF$_3$CO$_2$H),<br>[CDCl$_3$] | $n_D^{20.7}$ 1.4787,<br>bp 65–70° C./<br>1.3 mmHg |
| 2 | $^1$H-NMR δ (ppm) [solvent]:<br>2.68(s, 3H, COCH$_3$),<br>9.07(s, 1H),<br>9.48(s, 1H),<br>[CDCl$_3$]<br>$^{13}$C-NMR δ (ppm) [solvent]:<br>30.85(s, COCH$_3$),<br>120.34(q, J$_{F,C}$=276Hz, CF$_3$),<br>132.63(s, pyrimidine ring, 5-position),<br>151.26(q, J$_{F,C}$=37Hz, pyrimidine ring, 4-position),<br>157.14(s, pyrimidine ring),<br>159.42(s, pyrimidine ring),<br>197.19(s, C=O),<br>[CDCl$_3$] | bp 65–66° C.<br>3.5 mmHg |
| 3 | $^1$H-NMR δ (ppm) [solvent]:<br>1.28(s, 9H, C(CH$_3$)$_3$),<br>8.75(s, 1H, pyrimidine),<br>9.34(s, 1H, pyrimidine),<br>[CDCl$_3$]<br>$^{13}$C-NMR δ (ppm) [solvent]:<br>26.8(s, C(CH$_3$)$_3$),<br>45.2(s, C(CH$_3$)$_3$), | $n_D^{20.0}$ 1.4675 |

TABLE 1-2-continued

| Comp. No. | Spectral data | Physical Properties |
|---|---|---|
| | 123.0(t, J$_{F,C}$=291Hz, ClCF$_2$),<br>130.1(s, pyrimidine ring, 5-position),<br>154.9(t, J$_{F,C}$=31Hz, pyrimidine ring, 4-position),<br>155.2(s, pyrimidine ring),<br>158.3(s, pyrimidine ring),<br>207.2(s, C=O),<br>[CDCl$_3$]<br>$^{19}$F-NMR δ (ppm) [solvent]:<br>23.8(s, 2F, ClCF$_2$),<br>(ref. CF$_3$CO$_2$H),<br>[CDCl$_3$] | |
| 4 | $^1$H-NMR δ (ppm) [solvent]:<br>2.60(t, J=1Hz, 3H, COCH$_3$),<br>8.85(s, 1H, Pyrimidine ring),<br>9.37(s, 1H, Pyrimidine ring),<br>[CDCl$_3$] | $n_D^{20.1}$ 1.4335 |
| 5 | $^1$H-NMR δ (ppm) [solvent]:<br>0.97(s, 9H, C(CH$_3$)$_3$),<br>7.46(d, J=9Hz, 2H, Benzene ring),<br>7.65(d, J=9Hz, 2H, Benzene ring),<br>8.56(s, 1H, Pyrimidine ring),<br>9.30(s, 1H, Pyrimidine ring),<br>[CDCl$_3$]<br>$^{13}$C-NMR δ (ppm) [solvent]:<br>26.7(s, C(CH$_3$)$_3$),<br>45.9(s, C(CH$_3$)$_3$),<br>129.3(s, Benzene ring CH),<br>130.6(s, Benzene ring CH),<br>133.2(s, Pyrimidine ring, 5-position),<br>136.6(s, Benzene ring),<br>137.2(s, Benzene ring),<br>154.6(s, Pyrimidine ring, 6-position, CH),<br>158.4(s, Pyrimidine ring, 2-position, CH),<br>160.1(s, Pyrimidine ring, 4-Position),<br>212.1(s, COC(CH$_3$)$_3$),<br>[CDCl$_3$] | $n_D^{20.1}$ 1.5784 |
| 6 | $^1$H-NMR δ (ppm) [solvent]:<br>1.33(s, 9H, C(CH$_3$)$_3$),<br>7.49(d, J=9Hz, 2H, Benzene ring),<br>7.77(d, J=9Hz, 2H, Benzene ring),<br>8.42(s, 1H, Pyrimidine ring)<br>9.24(s, 1H, Pyrimidine ring)<br>[CDCl$_3$]<br>$^{13}$C-NMR δ (ppm) [solvent]:<br>30.0(s, C(CH$_3$)$_3$);<br>39.9(s, C(CH$_3$)$_3$);<br>129.4(s, Benzene ring CH),<br>131.5(s, Benzene ring CH),<br>131.5(s, Pyrimidine ring, 5-position)<br>135.4(s, Benzene ring),<br>141.1(s, Benzene ring),<br>155.2(s, Pyrimidine ring, 6-position)<br>158.1(s, Pyrimidine ring, 2-position, CH),<br>174.4(s, Pyrimidine ring, 4-position, CH),<br>194.7(s, CO),<br>[CDCl$_3$] | bp 75~77° C. |
| 7 | $^1$H-NMR δ (ppm) [solvent]:<br>1.11–1.47(m, 4H, cyclopropane ring (methylene))<br>2.10–2.50(m, 1H, cyclopropane ring(methine))<br>8.85(s, 1H, pyrimidine ring)<br>9.32(s, 1H, pyrimidine ring)<br>[CDCl$_3$] | $n_D^{20.5}$ 1.4998 |
| 8 | $^1$H-NMR δ (ppm) [solvent]:<br>1.06(s, 9H, C(CH$_3$)$_3$<br>6.89~7.37(m, 3H, Benzene ring)<br>8.67(s, 1H, Pyrimidine ring)<br>9.19(s, 1H, Pyrimidine ring)<br>[CDCl$_3$] | $n_D^{20.1}$ 1.5571 |
| 9 | $^1$H-NMR δ (ppm) [solvent]:<br>1.35(s, 9H, C(CH$_3$)$_3$)<br>6.83~7.08(m, 2H, Benzene ring)<br>7.70~7.75(m, 1H, Benzene ring)<br>8.17(s, 1H, Pyrimidine ring)<br>9.01(s, 1H, Pyrimidine ring) | mp 102–103° C. |

TABLE 1-2-continued

| Comp. No. | Spectral data | Physical Properties |
|---|---|---|
| 10 | [CDCl$_3$]<br>$^1$H-NMR δ (ppm) [solvent];<br>1.23(t, J=7Hz, 3H, CH$_2$CH$_3$)<br>2.88(q, J=7Hz, 2H, CH$_2$CH$_3$)<br>8.77(s, 1H, Pyrimidine ring)<br>9.32(s, 1H, Pyrimidine ring) | n$_D^{20.4}$ 1.4745 |
| 11 | [CDCl$_3$]<br>$^1$H-NMR δ (ppm) [solvent];<br>4.30(s, 2H, CH$_2$Br)<br>8.90(s, 1H, Pyrimidine ring)<br>9.38(s, 1H, Pyrimidine ring) | oil |
| 12 | [CDCl$_3$]<br>$^1$H-NMR δ (ppm) [solvent];<br>0.72~1.40(m, 4H, cyclo-propyl CH$_2$)<br>1.59~2.01(m, 1H, cyclo-propyl CH)<br>7.40(d, J=9Hz, 2H, Benzene ring)<br>7.62(d, J=9Hz, 2H, Benzene ring)<br>8.77(s, 1H, Pyrimidine ring)<br>9.22(s, 1H, Pyrimidine ring) | mp. 110–112° C. |
| 13 | [CDCl$_3$]<br>$^1$H-NMR δ (ppm) [solvent];<br>1.00(t, J=7Hz, 3H, CH$_2$CH$_2$CH$_3$)<br>1.74(tq, J=7, 7Hz, 2H, CH$_2$CH$_2$CH$_3$)<br>2.82(t, J=7Hz, 2H, CH$_2$CH$_2$CH$_3$)<br>8.77(s, 1H, Pyrimidine ring)<br>9.33(s, 1H, Pyrimidine ring) | n$_D^{19.7}$ 1.4770 |
| 14 | [CDCl$_3$]<br>$^1$H-NMR δ (ppm) [solvent];<br>0.97~1.46(m, 4H, cyclo-propyl CH$_2$)<br>2.00~2.42(m, 1H, cyclo-propyl CH)<br>8.84(s, 1H, Pyrimidine ring)<br>9.29(s, 1H, Pyrimidine ring) | n$_D^{20.5}$ 1.4732 |
| 15 | [CDCl$_3$]<br>$^1$H-NMR δ (ppm) [solvent];<br>1.16(s, 9H, C(CH$_3$)$_3$)<br>3.91(s, 3H, OCH$_3$)<br>7.00(d, J=9Hz, 2H, Benzene ring)<br>7.83(d, J=9Hz, 2H, Benzene ring)<br>8.47(s, 1H, Pyrimidine ring)<br>9.27(s, 1H, Pyrimidine ring) | mp 91–93° C. |
| 16 | [CDCl$_3$]<br>$^1$H-NMR δ (ppm) [solvent];<br>1.38(s, 9H, C(CH$_3$)$_3$)<br>3.60(s, 3H, OCH$_3$)<br>6.90~8.10(m, 4H, Benzene ring)<br>8.37(s, 1H, Pyrimidine ring)<br>9.19(s, 1H, Pyrimidine ring) | mp 71–73° C. |
| 17 | [CDCl$_3$]<br>$^1$H-NMR δ (ppm) [solvent];<br>2.61(t, J=1Hz, 3H, CH$_3$)<br>8.85(s, 1H, Pyrimidine ring)<br>9.41(s, 1H, Pyrimidine ring) | n$_D^{19.2}$ 1.4519 |
| 18 | [CDCl$_3$]<br>$^1$H-NMR δ (ppm) [solvent];<br>1.34(s, 9H, C(CH$_3$)$_3$)<br>2.42(s, 3H, CH$_3$)<br>7.30~7.80(m, 4H, Benzene ring)<br>8.46(s, 1H, Pyrimidine ring)<br>9.27(s, 1H, Pyrimidine ring) | mp 98–100° C. |
| 19 | [CDCl$_3$]<br>$^1$H-NMR δ (ppm) [solvent];<br>1.36(s, 9H, C(CH$_3$)$_3$)<br>2.73(s, 3H, CH$_3$)<br>6.80~7.80(m, 4H, Benzene ring)<br>8.45(s, 1H, Pyrimidine ring)<br>9.25(s, 1H, Pyrimidine ring) | mp 57–59° C. |
| 20 | [CDCl$_3$]<br>$^1$H-NMR δ (ppm) [solvent];<br>7.51(d, J=9Hz, 2H, Benzene ring)<br>7.72(d, J=9Hz, 2H, Benzene ring)<br>8.88(s, 1H, Pyrimidine ring)<br>9.50(s, 1H, Pyrimidine ring) | n$_D^{20.3}$ 1.5742 |
| 21 | $^1$H-NMR δ (ppm) [solvent];<br>7.19~7.69(m, 3H, Benzene ring)<br>8.78(s, 1H, Pyrimidine ring)<br>9.36(s, 1H, Pyrimidine ring) | n$_D^{20.5}$ 1.5837 |
| 22 | [CDCl$_3$]<br>$^1$H-NMR δ (ppm) [solvent];<br>2.62(s, 3H, CH$_3$)<br>8.79(s, 1H, Pyrimidine ring)<br>9.32(s, 1H, Pyrimidine ring) | n$_D^{19.9}$ 1.5069 |
| 23 | [CDCl$_3$]<br>$^1$H-NMR δ (ppm) [solvent];<br>7.34~7.84(m, 5H, Benzene ring)<br>8.76(s, 1H, Pyrimidine ring)<br>8.87(s, 1H, Pyrimidine ring) | n$_D^{20.1}$ 1.5571 |
| 24 | [CDCl$_3$]<br>$^1$H-NMR δ (ppm) [solvent];<br>6.95~8.00(m, 4H, Benzene ring)<br>8.82(s, 1H, Pyrimidine ring)<br>9.43(s, 1H, Pyrimidine ring) | mp 63–64° C. |
| 25 | [CDCl$_3$]<br>$^1$H-NMR δ (ppm) [solvent];<br>6.85~8.10(m, 4H, Benzene ring)<br>8.75(s, 1H, Pyrimidine ring)<br>9.34(s, 1H, Pyrimidine ring) | n$_D^{20.8}$ 1.5468 |
| 26 | [CDCl$_3$]<br>$^1$H-NMR δ (ppm) [solvent];<br>7.10~7.82(m, 4H, Benzene ring)<br>8.75(s, 1H, Pyrimidine ring)<br>9.46(s, 1H, Pyrimidine ring) | mp 40–42° C. |
| 27 | [CDCl$_3$]<br>$^1$H-NMR δ (ppm) [solvent];<br>7.17~7.76(m, 4H, Benzene ring)<br>8.77(s, 1H, Pyrimidine ring)<br>9.35(s, 1H, Pyrimidine ring) | n$_D^{19.8}$ 1.5612 |
| 28 | [CDCl$_3$]<br>$^1$H-NMR δ (ppm) [solvent];<br>7.34~7.76(m, 4H, Benzene ring)<br>8.79(s, 1H, Pyrimidine ring)<br>9.39(s, 1H, Pyrimidine ring) | n$_D^{19.8}$ 1.5756 |
| 29 | [CDCl$_3$]<br>$^1$H-NMR δ (ppm) [solvent];<br>7.37~7.91(m, 3H, Benzene ring)<br>9.00(s, 1H, Pyrimidine ring)<br>9.63(s, 1H, Pyrimidine ring) | mp 51–53° C. |
| 30 | [CDCl$_3$]<br>$^1$H-NMR δ (ppm) [solvent];<br>1.01(t, J=7Hz, 3H, CH$_2$CH$_2$CH$_3$)<br>1.77(tq, J=7.7Hz, 2H, CH$_2$CH$_2$CH$_3$)<br>2.96(t, J=7Hz, 2H, CH$_2$CH$_2$CH$_3$)<br>7.58(d, J=50Hz, 1H, CHFCl)<br>9.05(s, 1H, Pyrimidine ring)<br>9.30(s, 1H, Pyrimidine ring) | n$_D^{20.0}$ 1.5113 |
| 31 | [CDCl$_3$]<br>$^1$H-NMR δ (ppm) [solvent];<br>1.00(t, J=7Hz, 3H, CH$_2$CH$_2$CH$_3$)<br>1.77(tq, J=7.7Hz, 2H, CH$_2$CH$_2$CH$_3$)<br>2.95(t, J=7Hz, 2H, CH$_2$CH$_2$CH$_3$))<br>6.88(t, J=53Hz, 1H, CHF$_2$)<br>9.01(s, 1H, Pyrimidine ring)<br>9.30(s, 1H, Pyrimidine ring) | n$_D^{19.8}$ 1.4830 |
| 32 | [CDCl$_3$]<br>$^1$H-NMR δ (ppm) [solvent];<br>2.67(s, 3H, CH$_3$)<br>7.10–7.45(m, 4H, Benzene ring)<br>8.88(s, 1H, Pyrimidine ring)<br>9.46(s, 1H, Pyrimidine ring)<br>[CDCl$_3$] | n$_D^{20.4}$ 1.5588 |

TABLE 2-1

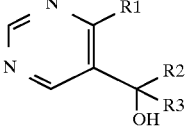

| Comp. No. | R1 | R2 | R3 |
|---|---|---|---|
| 101 | $CF_2Cl$ | Me | H |
| 102 | $CF_3$ | Me | H |
| 103 | $CF_2Cl$ | $Bu^{tert}$ | H |
| 104 | 4-Cl-Phenyl | $Bu^{tert}$ | H |
| 105 | $Bu^{tert}$ | 4-Cl-Phenyl | H |
| 106 | $CF_2Cl$ | $Pr^{cyclo}$ | H |
| 107 | $CF_2CF_3$ | Me | H |
| 108 | 2,4-$Cl_2$-Phenyl | $Bu^{tert}$ | H |
| 109 | $Bu^{tert}$ | 2,4-$Cl_2$-Phenyl | H |
| 110 | $CF_2Cl$ | Me | Me |
| 111 | $CF_2Cl$ | $Pr^n$ | H |
| 112 | $CF_2Cl$ | Et | H |
| 113 | 4-Cl-Phenyl | $Pr^{cyclo}$ | H |
| 114 | $CF_2Cl$ | $Pr^{iso}$ | H |
| 115 | $Bu^{tert}$ | 4-MeO-Phenyl | H |
| 116 | $Bu^{tert}$ | 2-MeO-Phenyl | H |
| 117 | $Bu^{tert}$ | 2-Me-Phenyl | H |
| 118 | $Bu^{tert}$ | 3-Me-Phenyl | H |
| 119 | $CF_2Cl$ | 4-Cl-Phenyl | H |
| 120 | $CF_2CF_2Cl$ | Me | H |
| 121 | $CF_2Cl$ | 2,4-$Cl_2$-Phenyl | H |
| 122 | $CF_2Br$ | Me | H |
| 123 | $CF_2Cl$ | Phenyl | H |
| 124 | $CF_2Cl$ | 4-F-Phenyl | H |
| 125 | $CF_2Cl$ | 2-F-Phenyl | H |
| 126 | $CF_2Cl$ | 2-Cl-Phenyl | H |
| 127 | $CF_2Cl$ | 3-Cl-Phenyl | H |
| 128 | $CF_2Cl$ | 3,4-$Cl_2$-Phenyl | H |
| 129 | $CF_2Cl$ | 3-F-Phenyl | H |

TABLE 2-2

| Comp. No. | Spectral data | Physical properties |
|---|---|---|
| 101 | $^1$H-NMR δ (ppm) [solvent]; 1.55(d, J=6Hz, 3H, C$\underline{H}_3$), 2.72(br s, 1H, O$\underline{H}$), 5.42(qd, J=6, 2Hz, 1H, C$\underline{H}$), 9.10(s, 1H), 9.20(s, 1H), [$CDCl_3$] | $n_D^{19.9}$ 1.4899 |
| 102 | $^1$H-NMR δ (ppm) [solvent]; 1.55(d, J=6Hz, 3H, C$\underline{H}_3$), 2.95(d, J=3Hz, 1H, O$\underline{H}$), 5.1~5.6(br m, 1H, C$\underline{H}$), 9.20(s, 1H), 9.27(s, 1H), [$CDCl_3$] | $n_D^{19.9}$ 1.4549 |
| 103 | MS(FAB+) m/z: 251 [M+H]$^+$, $^1$H-NMR δ (ppm) [solvent]; 0.93~0.99(m, 9H, C(C$\underline{H}_3)_3$), 3.03~3.85(br m, 1H, O$\underline{H}$), 5.08(s, 1H, C$\underline{H}$OH), 9.21(s, 1H, Pyrimidine ring), 9.25(s, 1H, Pyrimidine ring), [$CDCl_3$] | $n_D^{19.8}$ 1.4623 |
| 104 | $^1$H-NMR δ (ppm) [solvent]; 0.71(s, 9H, C(C$\underline{H}_3)_3$), 2.92(br, 1H, O$\underline{H}$), 4.84(s, 1H, C$\underline{H}$OH), 7.32(s, 4H, Benzene ring), 8.88(s, 1H, Pyrimidine ring), 8.98(s, 1H, Pyrimidine ring), [$CDCl_3$] MS(EI) m/z: 276(M$^+$, 41), 261(13), 243(8), 221(base peak), 219(99), 185(73), 57(95) | $n_D^{20.2}$ 1.5575 |

TABLE 2-2-continued

| Comp. No. | Spectral data | Physical properties |
|---|---|---|
| 105 | $^1$H-NMR δ (ppm) [solvent]; 1.43(s, 9H, C(C$\underline{H}_3)_3$), 4.39(br, 1H, O$\underline{H}$), 6.41(s, 1H, C$\underline{H}$OH), 7.15(s, 4H, Benzene ring), 8.30(s, 1H, Pyrimidine ring), 8.76(s, 1H, Pyrimidine ring), [$CDCl_3$] | $n_D^{20.2}$ 1.5474 |
| 106 | $^1$H-NMR δ (ppm) [solvent]; 0.49~0.74(m, 4H, cyclopropane(methylene)) 1.23~1.44(m, 4H, cyclopropane(methine)) 3.00(br, 1H, O$\underline{H}$), 4.70~4.89(m, 1H, φC$\underline{H}$OH) 9.11(s, 1H, Pyrimidine ring), 9.19(s, 1H, Pyrimidine ring), [$CDCl_3$] | $n_D^{20.5}$ 1.5020 |
| 107 | $^1$H-NMR δ (ppm) [solvent]; 1.55(d, J=6Hz, 3H, C$\underline{H}_3$) 2.4~3.0(br s, 1H, O$\underline{H}$) 5.1~5.6(m, 1H, C$\underline{H}$) 9.12(s, 1H, Pyrimidine ring) 9.22(s, 1H, Pyrimidine ring) [$CDCl_3$] | $n_D^{20.1}$ 1.4347 |
| 108 | $^1$H-NMR δ (ppm) [solvent]; 0.74(s, 9H, C(C$\underline{H}_3)_3$) 3.23(br s, 1H, O$\underline{H}$) 4.22(s, 1H, φC$\underline{H}$) 6.92~7.26(m, 3H, Benzene ring) 8.85(s, 1H, Pyrimidine ring) 8.97(s, 1H, Pyrimidine ring) [$CDCl_3$] | $n_D^{19.5}$ 1.5554 |
| 109 | $^1$H-NMR δ (ppm) [solvent]; 1.43(s, 9H, C(C$\underline{H}_3)_3$) 4.83(br s, 1H, O$\underline{H}$) 6.45(s, 1H, φC$\underline{H}$) 6.76~7.27(m, 3H, Benzene ring) 8.24(s, 1H, Pyrimidine ring) 8.76(s, 1H, Pyrimidine ring) [$CDCl_3$] | $n_D^{19.3}$ 1.5464 |
| 110 | $^1$H-NMR δ (ppm) [solvent]; 1.78(s, 6H, C$\underline{H}_3$ × 2), 3.05(br. s, 1H, O$\underline{H}$) 9.17(s, 1H, Pyrimidine ring) 9.32(s, 1H, Pyrimidine ring) [$CDCl_3$] | $n_D^{20.6}$ 1.4982 |
| 111 | $^1$H-NMR δ (ppm) [solvent]; 0.70~1.19(m, 3H, C$\underline{H}_3$) 1.19~2.00(m, 4H, CHC$\underline{H}_2$C$\underline{H}_2$CH$_3$) 2.4~3.1(br s, 1H, O$\underline{H}$) 5.0~5.5(m, 1H, C$\underline{H}$) 9.09(s, 1H, Pyrimidine ring) 9.12(s, 1H, Pyrimidine ring) [$CDCl_3$] | $n_D^{19.8}$ 1.4798 |
| 112 | $^1$H-NMR δ (ppm) [solvent]; 1.05(t, J=7Hz, 3H, CH$_2$C$\underline{H}_3$) 1.74(br q, J=7Hz, 2H, CHC$\underline{H}_2$CH$_3$) 2.91(d, J=3Hz, 1H, O$\underline{H}$) 4.85~5.35(m, 1H, C$\underline{H}$) 9.06(s, 1H, Pyrimidine ring) 9.10(s, 1H, Pyrimidine ring) [$CDCl_3$] | $n_D^{19.9}$ 1.4845 |
| 113 | $^1$H-NMR δ (ppm) [solvent]; 0.21~0.74(m, 4H, cyclo-propyl C$\underline{H}_2$) 0.94~1.46(m, 1H, cyclo-propyl C$\underline{H}$) 3.10(br. s, 1H, O$\underline{H}$) 4.25(d, J=7Hz, 1H, φC$\underline{H}$) 7.33(d, J=9Hz, 2H, Benzene ring) 7.51(d, J=9Hz, 2H, Benzene ring) 8.96(s, 1H, Pyrimidine ring) 9.01(s, 1H, Pyrimidine ring) [$CDCl_3$] | mp 142–144° C. |
| 114 | $^1$H-NMR δ (ppm) [solvent]; 0.99(t, J=6Hz, 6H, CH(C$\underline{H}_3)_2$) 2.00(qq, J=6Hz, 1H, C$\underline{H}$(CH$_3)_2$) 2.8~3.8(br s, 1H, O$\underline{H}$) | $n_D^{19.8}$ 1.4822 |

TABLE 2-2-continued

| Comp. No. | Spectral data | Physical properties |
|---|---|---|
| | 4.99(br d, 1H, C$\underline{H}$OH)<br>9.10(s, 2H, Pyrimidine ring)<br>[CDCl$_3$] | |
| 115 | $^1$H-NMR δ (ppm) [solvent];<br>1.41(s, 9H, C(C$\underline{H}_3$)$_3$)<br>3.78(s, 3H, OC$\underline{H}_3$)<br>4.80(br s, 1H, O$\underline{H}$)<br>6.48(br s, 1H, C$\underline{H}$)<br>6.84(d, $\underline{J}$=9Hz, 2H, Benzene ring)<br>7.20(d, $\underline{J}$=9Hz, 2H, Benzene ring)<br>8.58(s, 1H, Pyrimidine ring)<br>8.88(s, 1H, Pyrimidine ring)<br>[CDCl$_3$] | mp 90–92° C. |
| 116 | $^1$H-NMR δ (ppm) [solvent];<br>1.45(s, 9H, C(C$\underline{H}_3$)$_3$)<br>3.61(br s, 1H, O$\underline{H}$)<br>3.81(s, 3H, OC$\underline{H}_3$)<br>6.6~7.6(m, 5H, C$\underline{H}$ + Benzene ring)<br>8.67(s, 1H, Pyrimidine ring)<br>9.04(s, 1H, Pyrimidine ring)<br>[CDCl$_3$] | mp 102–104° C. |
| 117 | $^1$H-NMR δ (ppm) [solvent];<br>1.36(s, 9H, C(C$\underline{H}_3$)$_3$)<br>2.34(s, 3H, C$\underline{H}_3$)<br>4.25(br s, 1H, O$\underline{H}$)<br>6.56(s, 1H, C$\underline{H}$)<br>6.9~7.6(m, 4H, Benzene ring)<br>8.63(s, 1H, Pyrimidine ring)<br>8.90(s, 1H, Pyrimidine ring)<br>[CDCl$_3$] | mp 125–127° C. |
| 118 | $^1$H-NMR δ (ppm) [solvent];<br>1.43(s, 9H, C(C$\underline{H}_3$)$_3$)<br>2.30(s, 3H, C$\underline{H}_3$)<br>4.8~5.3(m, 1H, O$\underline{H}$)<br>6.45(br s, 1H, C$\underline{H}$)<br>6.8~7.5(m, 4H, Benzene ring)<br>8.48(s, 1H, Pyrimidine ring)<br>8.85(s, 1H, Pyrimidine ring)<br>[CDCl$_3$] | $n_D^{21.5}$ 1.5574 |
| 119 | $^1$H-NMR δ (ppm) [solvent];<br>3.40(br s, 1H, O$\underline{H}$)<br>6.34(s, 1H, φC$\underline{H}$)<br>7.29(s, 4H, Benzene ring)<br>9.09(s, 1H, Pyrimidine ring)<br>9.14(s, 1H, Pyrimidine ring)<br>[CDCl$_3$] | $n_D^{20.3}$ 1.5563 |
| 120 | $^1$H-NMR δ (ppm) [solvent];<br>1.53(d, $\underline{J}$=6Hz, 3H, CHC$\underline{H}_3$)<br>2.62(br s, 1H, O$\underline{H}$)<br>5.07~5.58(m, 1H, C$\underline{H}$CH$_3$)<br>9.10(s, 1H, Pyrimidine ring)<br>9.18(s, 1H, Pyrimidine ring)<br>[CDCl$_3$] | $n_D^{20.1}$ 1.4616 |
| 121 | $^1$H-NMR δ (ppm) [solvent];<br>3.42(br d, $\underline{J}$=5Hz, 1H, O$\underline{H}$)<br>6.58(d, $\underline{J}$=5Hz, 1H, φC$\underline{H}$)<br>7.30~7.45(m, 3H, Benzene ring)<br>8.82(s, 1H, Pyrimidine ring)<br>9.20(s, 1H, Pyrimidine ring)<br>[CDCl$_3$] | mp 141–142° C. |
| 122 | $^1$H-NMR δ (ppm) [solvent];<br>1.57(d, $\underline{J}$=6Hz, 3H, CHC$\underline{H}_3$)<br>3.12~3.78(br s, 1H, O$\underline{H}$)<br>5.41(d, 1, $\underline{J}$=3, 6Hz, 1$\underline{H}$, C$\underline{H}$CH$_3$)<br>9.07(s, 1H, Pyrimidine ring)<br>9.17(s, 1H, Pyrimidine ring)<br>[CDCl$_3$] | $n_D^{20.1}$ 1.5160 |
| 123 | $^1$H-NMR δ (ppm) [solvent];<br>4.79~5.04(m, 1H, O$\underline{H}$)<br>6.23(br s, 1H, φC$\underline{H}$)<br>7.17(br s, 5H, Benzene ring)<br>8.82(s, 1H, Pyrimidine ring)<br>8.97(s, 1H, Pyrimidine ring)<br>[CDCl$_3$] | $n_D^{20.0}$ 1.5566 |
| 124 | $^1$H-NMR δ (ppm) [solvent];<br>3.68(d, $\underline{J}$=6Hz, 1H, O$\underline{H}$)<br>6.20~6.40(m, 1H, C$\underline{H}$OH)<br>6.90~7.53(m, 4H, Benzene ring)<br>9.06(s, 2H, Pyrimidine ring)<br>[CDCl$_3$] | $n_D^{20.5}$ 1.5394 |
| 125 | $^1$H-NMR δ (ppm) [solvent];<br>3.38–4.08(br s, 1H, O$\underline{H}$)<br>6.55(s, 1H, C$\underline{H}$OH)<br>6.68–7.58(m, 4H, Benzene ring)<br>9.06(s, 2H, Pyrimidine ring)<br>[CDCl$_3$] | $n_D^{19.7}$ 1.5434 |
| 126 | $^1$H-NMR δ (ppm) [solvent];<br>4.20–4.41(br m, 1H, O$\underline{H}$)<br>6.53–6.67(m, 1H, C$\underline{H}$OH)<br>7.12–7.56(m, 4H, Benzene ring)<br>8.73(s, 1H, Pyrimidine ring)<br>9.00(s, 1H, Pyrimidine ring)<br>[CDCl$_3$] | $n_D^{20.5}$ 1.5378 |
| 127 | $^1$H-NMR δ (ppm) [solvent];<br>4.22–4.43(br m, 1H, O$\underline{H}$)<br>6.21–6.35(m, 1H, C$\underline{H}$OH)<br>7.06–7.35(m, 4H, Benzene ring)<br>8.99(s, 1H, Pyrimidine ring)<br>9.02(s, 1H, Pyrimidine ring)<br>[CDCl$_3$] | $n_D^{19.8}$ 1.5402 |
| 128 | $^1$H-NMR δ (ppm) [solvent];<br>3.10–3.50(br m, 1H, O$\underline{H}$)<br>6.23–6.32(m, 1H, C$\underline{H}$OH)<br>6.97–7.48(m, 3H, Benzene ring)<br>8.98(s, 1H, Pyrimidine ring)<br>9.10(s, 1H, Pyrimidine ring)<br>[CDCl$_3$] | mp 66–68° C. |
| 129 | $^1$H-NMR δ (ppm) [solvent];<br>3.40–3.80(br s, 1H, O$\underline{H}$)<br>6.33(s, 1H, C$\underline{H}$OH)<br>6.74–7.60(m, 4H, Benzene ring)<br>9.01(s, 1H, Pyrimidine ring)<br>9.09(s, 1H, Pyrimidine ring)<br>[CDCl$_3$] | $n_D^{19.7}$ 1.5438 |

TABLE 3-1

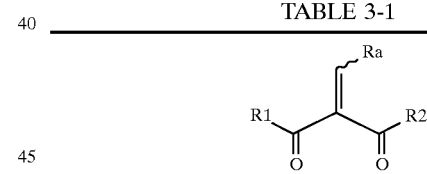

| Comp. No. | R1, R2, Ra; | Physical properties |
|---|---|---|
| 201 | CF$_3$, Me, OMe; | bp 93–97° C./3.5 Torr |
| 202 | CF$_3$, Me, OEt; | bp 82–83° C./0.2 Torr |
| 203 | CF$_2$Cl, Me, OEt; | bp 95–118° C./1.6 Torr |
| 204 | CF$_2$Cl, Bu$^{tert}$, OEt; | bp 105–107° C./2.0 Torr |
| 205 | CF$_2$CF$_3$, Me, OEt; | bp 98° C./2.2 Torr |
| 206 | 4-Cl-Phenyl, Bu$^{tert}$, NMe$_2$; | mp 102–104° C. |
| 207 | CF$_2$Cl, Pr$^{cyclo}$, OEt; | $n_D^{20.6}$ 1.4787 |
| 208 | 2,4-Cl$_2$-Phenyl, Bu$^{tert}$, NMe$_2$; | $n_D^{19.9}$ 1.5437 |
| 209 | 4-Cl-Phenyl, Me, NMe$_2$; | $n_D^{20.0}$ 1.5964 |
| 210 | CF$_2$Cl, Et, OEt; | bp 117–120° C./2.3 Torr |
| 211 | 4-Cl-Phenyl, Pr$^{cyclo}$, NMe$_2$; | mp 37–39° C. |
| 212 | 4-MeO-Phenyl, Bu$^{tert}$, NMe$_2$; | mp 93–95° C. |
| 213 | CF$_2$Cl, Pr$^{iso}$, OEt; | bp 105–115° C./1.7 Torr |
| 214 | 2-Me-Phenyl, Bu$^{tert}$, NMe$_2$; | mp 90–92° C. |
| 215 | 3-Me-Phenyl, Bu$^{tert}$, NMe$_2$; | mp 83–86° C. |
| 216 | 2-MeO-Phenyl, Bu$^{tert}$, NMe$_2$; | mp 109–112° C. |
| 217 | CF$_2$CF$_2$Cl, Me, OEt; | bp 110–115° C./2.1 Torr |
| 218 | CF$_2$Cl, 4-Cl-Phenyl, NMe$_2$; | bp 79–81° C. |
| 219 | CF$_2$Cl, Phenyl, OEt; | $n_D^{20.1}$ 1.5395 |
| 220 | CF$_2$Cl, 4-F-Phenyl, OEt; | $n_D^{20.9}$ 1.5233 |
| 221 | CF$_2$Cl, 2-F-Phenyl, OEt; | $n_D^{20.0}$ 1.3808 |
| 222 | CF$_2$Cl, 3-F-Phenyl, OEt; | $n_D^{19.7}$ 1.4900 |
| 223 | CF$_2$Cl, 2-Cl-Phenyl, OEt; | $n_D^{19.9}$ 1.5306 |

TABLE 3-1-continued $$\text{R1-C(=O)-C(=CHRa)-C(=O)-R2}$$

| Comp. No. | R1, R2, Ra; | Physical properties |
|---|---|---|
| 224 | $CF_2Cl$, 3-Cl-Phenyl, OEt; | $n_D^{19.9}$ 1.5578 |
| 225 | $CF_2Cl$, 3,4-$Cl_2$-Phenyl, OEt; | $n_D^{19.9}$ 1.15578 |
| 226 | CHFCl, $Pr^n$, OEt; | $n_D^{19.8}$ 1.4770 |
| 227 | $CF_2H$, $Pr^n$, OEt; | $n_D^{19.9}$ 1.4580 |
| 228 | $CF_2Cl$, 2-Me-Phenyl, OEt; | $n_D^{20.3}$ 1.5350 |

TABLE 3-2

$$\text{R1-C(=O)-CH_2-C(=O)-R2}$$

| Comp. No. | R1, R2; | Physical properties |
|---|---|---|
| 301 | $CF_2Cl$, $Bu^{tert}$; | bp 54–57° C./5.0 Torr |
| 302 | $CF_2CF_3$, $Bu^{tert}$; | $^1$H-NMR δ (ppm) [solvent]; 1.22(s, 9H, t-Bu), 6.05(s, 1H, C$\underline{H}$), 13.0~14.0(br s, 1H, O$\underline{H}$, [CDCl$_3$] liquid. |
| 303 | 4-Cl-Phenyl, $Bu^{tert}$; | $n_D^{20.0}$ 1.5012 |
| 304 | $CF_2CF_3$, Me; | bp 105–115° C. |
| 305 | $CF_2Cl$, $Pr^{cyclo}$; | $n_D^{20.6}$ 1.4788 |
| 306 | 2,4-$Cl_2$-Phenyl, $Bu^{tert}$; | $n_D^{19.9}$ 1.5690 |
| 307 | $CF_2Cl$, Et; | bp 74–78° C./20 Torr |
| 308 | $CF_2Cl$, $Pr^n$; | bp 84° C./17 Torr |
| 309 | 4-Cl-Phenyl, $Pr^{cyclo}$; | mp 73–75° C. |
| 310 | $CF_2Cl$, $Pr^{iso}$; | bp 42–43° C./3.0 Torr |
| 311 | 4-MeO-Phenyl, $Bu^{tert}$; | mp 50–52° C. |
| 312 | 2-Me-Phenyl, $Bu^{tert}$; | $n_D^{21.5}$ 1.4882 |
| 313 | 3-Me-Phenyl, $Bu^{tert}$; | $n_D^{21.4}$ 1.5564 |
| 314 | 4-$CF_3$-Phenyl, $Bu^{tert}$; | mp 55–58° C. |
| 315 | 2-F-Phenyl, $Bu^{tert}$; | $n_D^{20.3}$ 1.5488 |
| 316 | 2-MeO-Phenyl, $Bu^{tert}$; | $n_D^{20.4}$ 1.5622 |
| 317 | 2,4-$Cl_2$-Phenyl, Me; | mp 30–31° C. |
| 318 | $CF_2Cl$, 4-Cl-Phenyl; | mp 50–51° C. |
| 319 | 3-$CF_3$-Phenyl, $Bu^{tert}$; | $^1$H-NMR δ (ppm) [solvent]; 1.27(s, 9H, t-Bu), 6.36(s, 1H, olefin), 7.30~8.40(m, 4H, benzene ring), 16.56(s, 1H, enol O$\underline{H}$) [CDCl$_3$] liquid. |
| 320 | $CF_2Cl$, 1-Me-$Pr^{cyclo}$; | bp 59–63° C./2.0 Torr |
| 321 | $CF_2CF_2Cl$, Me; | bp 120–128° C. |
| 322 | $CF_2Cl$, 2,4-$Cl_2$-Phenyl; | $n_D^{21.7}$ 1.5828 |
| 323 | $CF_2Br$, Me; | bp 100–105° C. |
| 324 | $CF_2Cl$, 4-F-Phenyl; | mp 48–50° C. |
| 325 | $CF_2Cl$, Phenyl; | mp 29–30° C. |
| 326 | $CF_2Cl$, 2-F-Phenyl; | $n_D^{19.9}$ 1.5554 |
| 327 | $CF_2Cl$, 3-F-Phenyl; | mp 46–48° C. |
| 328 | $CF_2Cl$, 2-Cl-Phenyl; | $n_D^{19.9}$ 1.5630 |
| 329 | $CF_2Cl$, 3-Cl-Phenyl; | $n_D^{19.9}$ 1.5807 |
| 330 | $CF_2Cl$, 3,4-$Cl_2$-Phenyl; | mp 41–43° C. |
| 331 | CHFCl, $Pr^n$; | bp 94–100° C./20 Torr |
| 332 | $CF_2H$, $Pr^n$; | bp 74–76° C./20 Torr |
| 333 | $CF_2Cl$, 2-Me-Phenyl; | $n_D^{19.9}$ 1.5566 |

Tables 4-1, 4-2 and 4-3 show the compounds of the present invention which can be synthesized in accordance with the above-mentioned schemes and Examples, including those synthesized in the preceding Examples. However, it should be understood that the present invention is by no means restricted by such specific examples.

TABLE 4-1

Structures shown with a pyrimidine-substituted enone framework bearing various substituents at the vinyl position:

- $CF_2Cl$
- $CF_3$
- $CFCl_2$
- $CCl_3$
- $CF_2CF_2H$
- $CFHCF_2Cl$
- $CH_2CF_3$
- $CF_2CF_2CF_3$
- $CF_2CF_2CF_2Cl$
- $C_2H_5$ each attached to the common skeleton:

$$\text{(pyrimidinyl)-C(X)=C(-C(=O)R2)-}$$

TABLE 4-1-continued

TABLE 4-1-continued
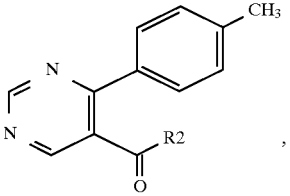
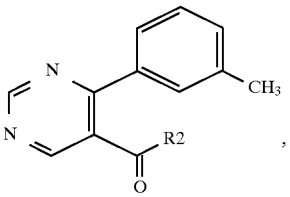
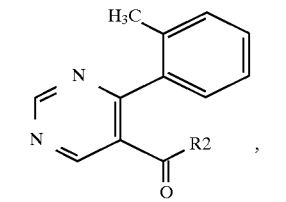
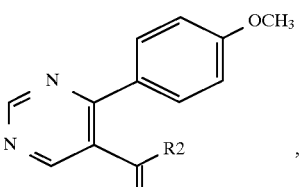
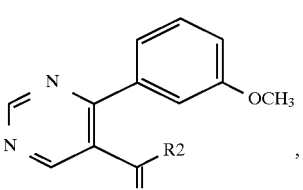
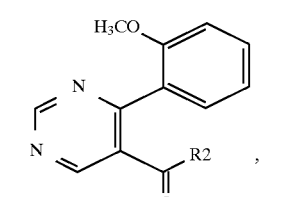
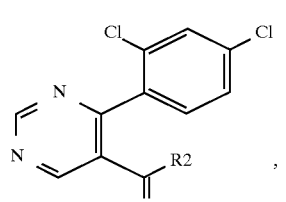
TABLE 4-1-continued
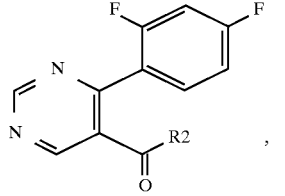
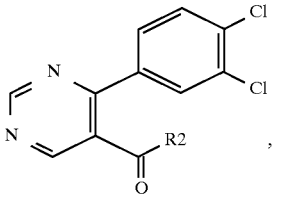
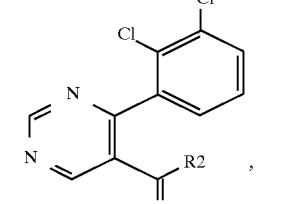
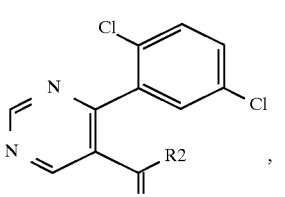
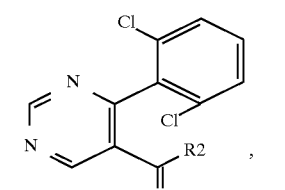
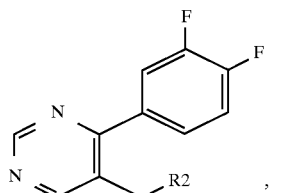

TABLE 4-1-continued
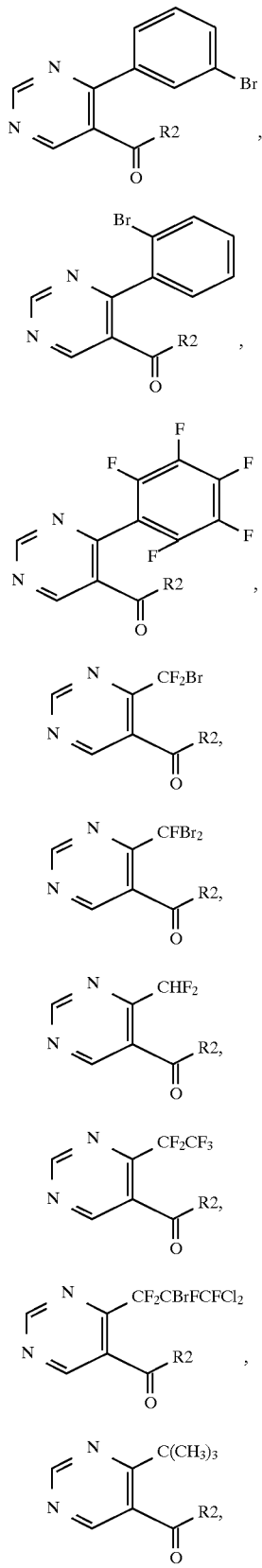
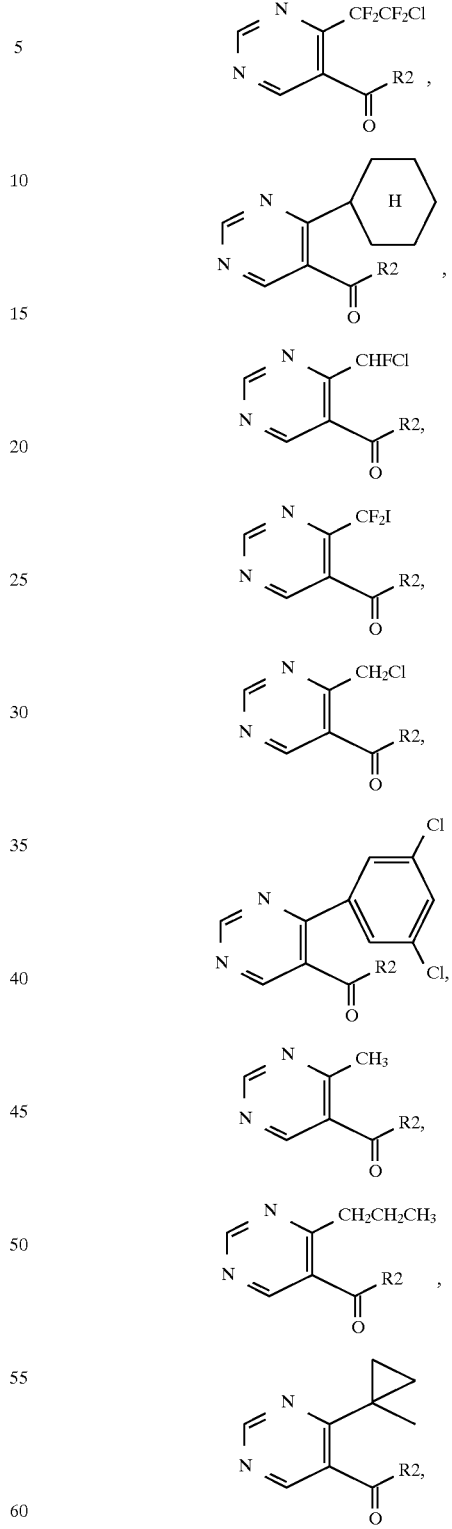
wherein R2 is selected from the following group.
| R2 |
|---|
| Me, Et, Pr, Pr$^{iso}$, Pr$^{cyclo}$, Bu, Bu$^{sec}$, Bu$^{iso}$, Bu$^{tert}$, Bu$^{cyclo}$, Pn, Pn$^{neo}$, Pn$^{iso}$, Pn$^{cyclo}$, Hex, Hex$^{cyclo}$, |

TABLE 4-1-continued

C(Me)₂(CH₂F), CF₃, CH₂CF₃, Ph, 2-Cl-Ph,
3-Cl-Ph, 4-Cl-Ph, 2-F-Ph, 3-F-Ph, 4-F-Ph, 2-CF₃-Ph,
3-CF₃-Ph, 4-CF₃-Ph, 2-Me-Ph, 3-Me-Ph, 4-Me-Ph,
2-MeO-Ph, 3-MeO-Ph, 4-MeO-Ph, 2-CF₃O-Ph,
3-CF₃O-Ph, 4-CF₃O-Ph, 2-Br-Ph, 3-Br-Ph, 4-Br-Ph,
2,4-Cl₂-Ph, 3,4-Cl₂-Ph, 2,6-Cl₂-Ph, 2-F-4-Cl-Ph,
2,4-F₂-Ph, 3,4-F₂-Ph, 2,5-Cl₂-Ph, 2,3-Cl₂-Ph,
2,6-F₂-Ph, CH₂Br
3,5-Cl₂-Ph, 2-Me-4-Cl-Ph, 2-Me-4-F-Ph, 1-MeSO₂-Et,
1-Me-Pr$^{cyclo}$, 1-F—Pr$^{cyclo}$, 1-Cl—Pr$^{cyclo}$, 1-MeS—Pr$^{cyclo}$,
1-EtS—Pr$^{cyclo}$, CH₂Cl, CF(Me)₂, 1-Pr$^{cyclo}$-Et,
CH₂CH=CH₂, CH₂C≡CH, CH(Me)C≡CH, C(Me)₂C≡CH, CH(Me)CH=CH₂, 4-Bu$^{tert}$-Ph, 3-Bu$^{tert}$-Ph,
2-Bu$^{tert}$-Ph, 2-Et-Ph, 3-Et-Ph, 4-Et-Ph, 2-Pr-Ph, 3-Pr-Ph,
4-Pr-Ph, 2-Bu-Ph, 3-Bu-Ph, 4-Bu-Ph, 2-EtO-Ph,
2-Pr$^{iso}$O-Ph, 2-PrO-Ph,

TABLE 4-2

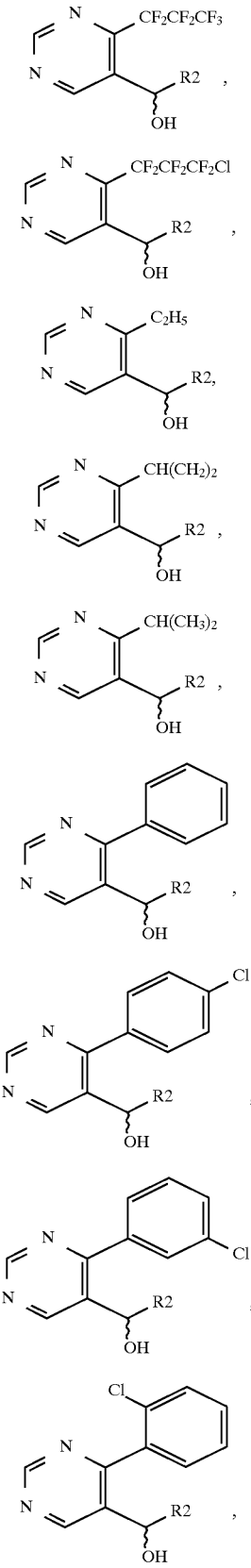

TABLE 4-2-continued

TABLE 4-2-continued
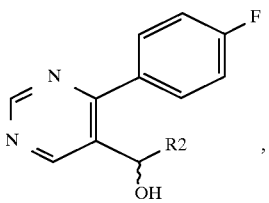
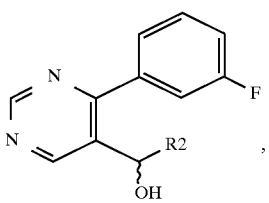
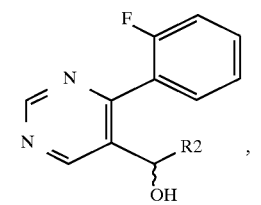
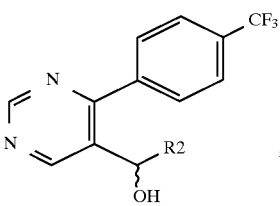
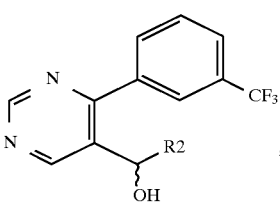
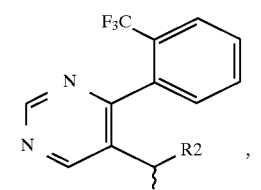
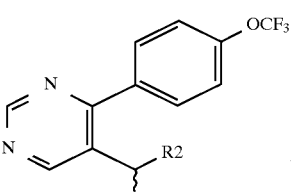
TABLE 4-2-continued
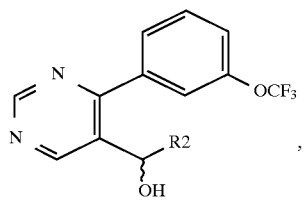
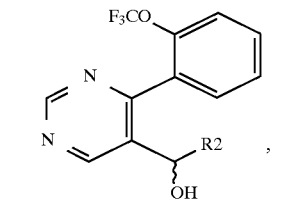
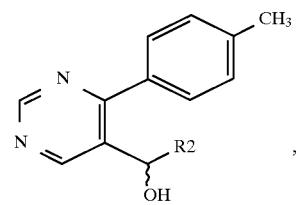
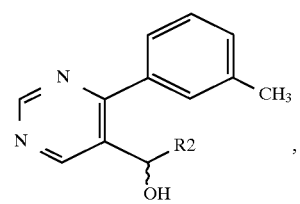
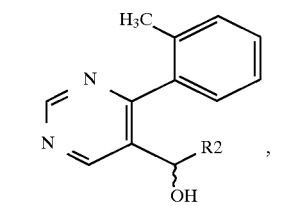
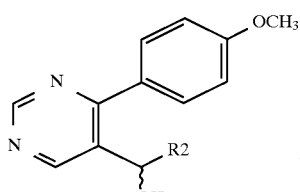
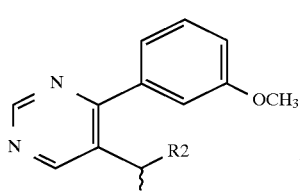

TABLE 4-2-continued
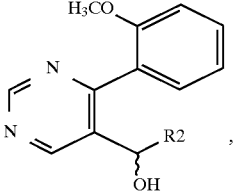
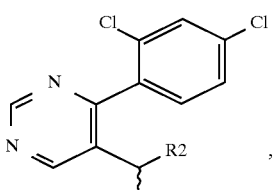
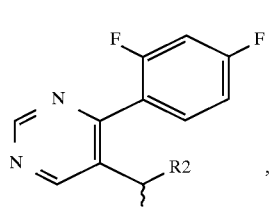
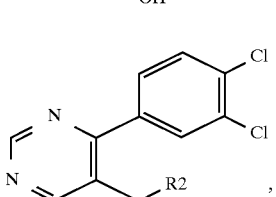
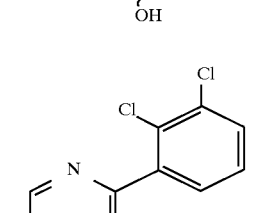
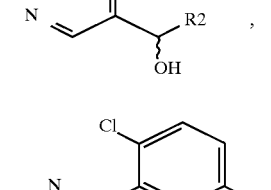
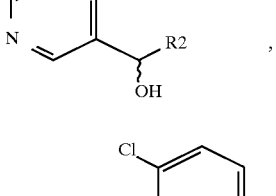
TABLE 4-2-continued
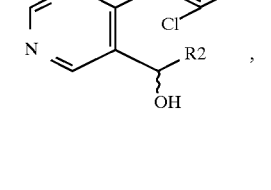
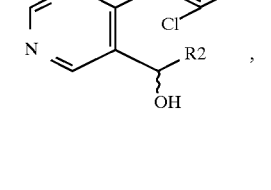
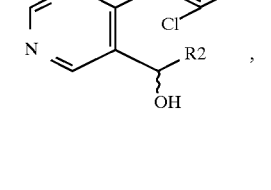
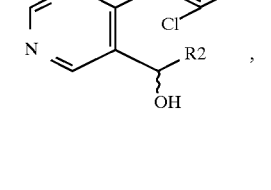
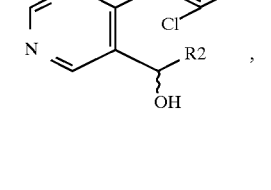
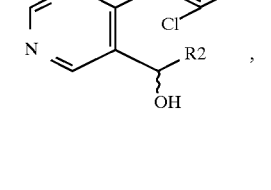
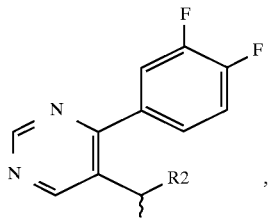
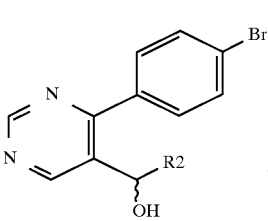

TABLE 4-2-continued

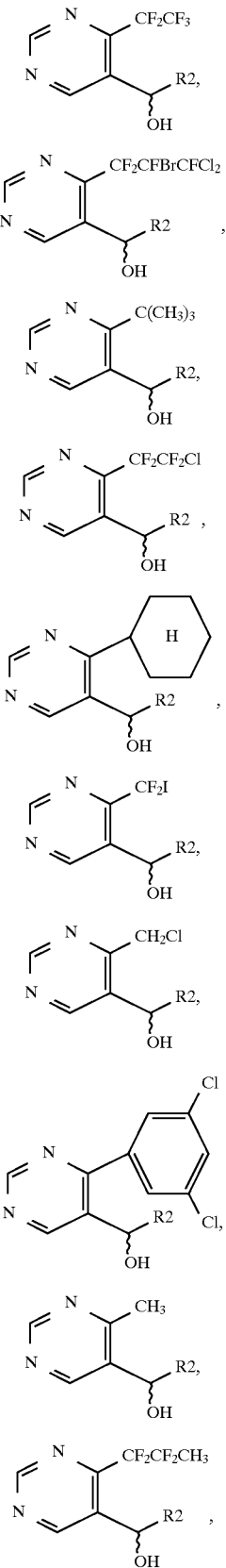

TABLE 4-2-continued

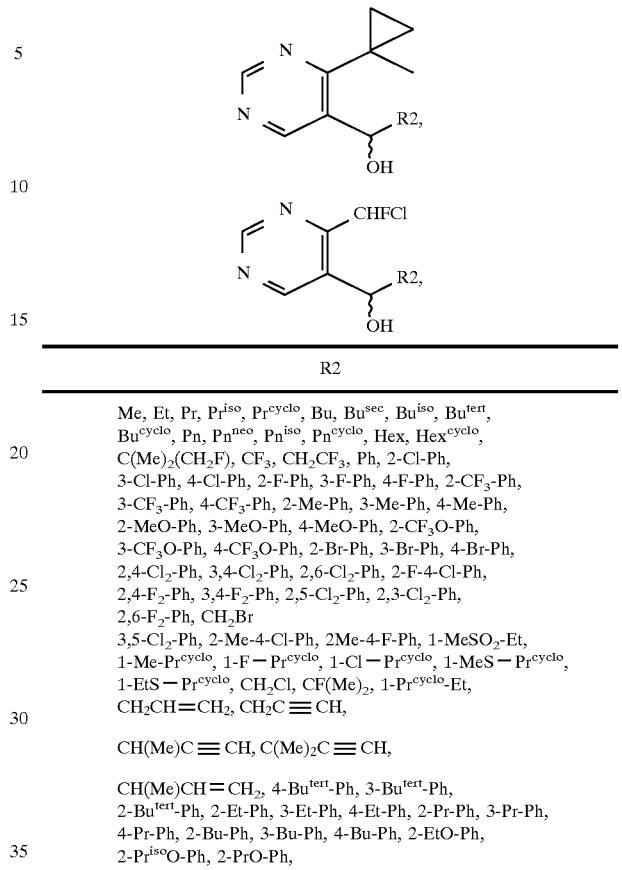

| R2 |
|---|
| Me, Et, Pr, Pr$^{iso}$, Pr$^{cyclo}$, Bu, Bu$^{sec}$, Bu$^{iso}$, Bu$^{tert}$, Bu$^{cyclo}$, Pn, Pn$^{neo}$, Pn$^{iso}$, Pn$^{cyclo}$, Hex, Hex$^{cyclo}$, C(Me)$_2$(CH$_2$F), CF$_3$, CH$_2$CF$_3$, Ph, 2-Cl-Ph, 3-Cl-Ph, 4-Cl-Ph, 2-F-Ph, 3-F-Ph, 4-F-Ph, 2-CF$_3$-Ph, 3-CF$_3$-Ph, 4-CF$_3$-Ph, 2-Me-Ph, 3-Me-Ph, 4-Me-Ph, 2-MeO-Ph, 3-MeO-Ph, 4-MeO-Ph, 2-CF$_3$O-Ph, 3-CF$_3$O-Ph, 4-CF$_3$O-Ph, 2-Br-Ph, 3-Br-Ph, 4-Br-Ph, 2,4-Cl$_2$-Ph, 3,4-Cl$_2$-Ph, 2,6-Cl$_2$-Ph, 2-F-4-Cl-Ph, 2,4-F$_2$-Ph, 3,4-F$_2$-Ph, 2,5-Cl$_2$-Ph, 2,3-Cl$_2$-Ph, 2,6-F$_2$-Ph, CH$_2$Br 3,5-Cl$_2$-Ph, 2-Me-4-Cl-Ph, 2Me-4-F-Ph, 1-MeSO$_2$-Et, 1-Me-Pr$^{cyclo}$, 1-F—Pr$^{cyclo}$, 1-Cl—Pr$^{cyclo}$, 1-MeS—Pr$^{cyclo}$, 1-EtS—Pr$^{cyclo}$, CH$_2$Cl, CF(Me)$_2$, 1-Pr$^{cyclo}$-Et, CH$_2$CH═CH$_2$, CH$_2$C≡CH, CH(Me)C≡CH, C(Me)$_2$C≡CH, CH(Me)CH═CH$_2$, 4-Bu$^{tert}$-Ph, 3-Bu$^{tert}$-Ph, 2-Bu$^{tert}$-Ph, 2-Et-Ph, 3-Et-Ph, 4-Et-Ph, 2-Pr-Ph, 3-Pr-Ph, 4-Pr-Ph, 2-Bu-Ph, 3-Bu-Ph, 4-Bu-Ph, 2-EtO-Ph, 2-Pr$^{iso}$O-Ph, 2-PrO-Ph, |

TABLE 4-3

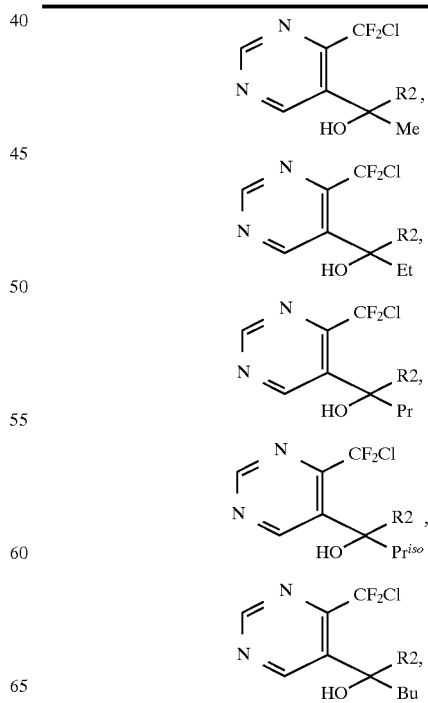

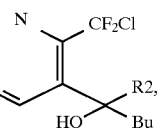

TABLE 4-3-continued

TABLE 4-3-continued

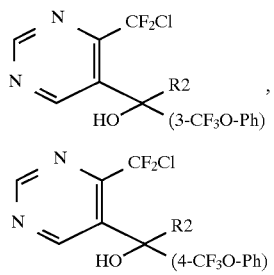

R2

Me, Et, Pr, Pr$^{iso}$, Pr$^{cyclo}$, Bu, Bu$^{sec}$, Bu$^{iso}$, Bu$^{tert}$,
Bu$^{cyclo}$, Pn, Pn$^{neo}$, Pn$^{iso}$, Pn$^{cyclo}$, Hex, Hex$^{cyclo}$,
C(Me)$_2$(CH$_2$F), CF$_3$, CH$_2$CF$_3$, Ph, 2-Cl-Ph,
3-Cl-Ph, 4-Cl-Ph, 2-F-Ph, 3-F-Ph, 4-F-Ph, 2-CF$_3$-Ph,
3-CF$_3$-Ph, 4-CF$_3$-Ph, 2-Me-Ph, 3-Me-Ph, 4-Me-Ph,
2-MeO-Ph, 3-MeO-Ph, 4-MeO-Ph, 2-CF$_3$O-Ph,
3-CF$_3$O-Ph, 4-CF$_3$O-Ph, 2-Br-Ph, 3-Br-Ph, 4-Br-Ph,
2,4-Cl$_2$-Ph, 3,4-Cl$_2$-Ph, 2,6-Cl$_2$-Ph, 2-F-4-Cl-Ph,
2,4-F$_2$-Ph, 3,4-F$_2$-Ph, 2,5-Cl$_2$-Ph, 2,3-Cl$_2$-Ph,
2,6-F$_2$-Ph, CH$_2$Br
3,5-Cl$_2$-Ph, 2-Me-4-Cl-Ph, 2Me-4-F-Ph, 1-MeSO$_2$-Et,
1-Me-Pr$^{cyclo}$, 1-F—Pr$^{cyclo}$, 1-Cl—Pr$^{cyclo}$, 1-MeS—Pr$^{cyclo}$,
1-EtS—Pr$^{cyclo}$, CH$_2$Cl, CF(Me)$_2$, 1-Pr$^{cyclo}$-Et,
CH$_2$CH=CH$_2$, CH$_2$C≡CH, CH(Me)C≡CH, C(Me)$_2$C≡CH, CH(Me)CH=CH$_2$, 4-Bu$^{tert}$-Ph, 3-Bu$^{tert}$-Ph,
2-Bu$^{tert}$-Ph, 2-Et-Ph, 3-Et-Ph, 4-Et-Ph, 2-Pr-Ph, 3-Pr-Ph,
4-Pr-Ph, 2-Bu-Ph, 3-Bu-Ph, 4-Bu-Ph, 2-EtO-Ph,
2-Pr$^{iso}$O-Ph, 2-PrO-Ph, The symbols in the tables have the following meanings.

Ph: Phenyl
Me: CH$_3$
Et: C$_2$H$_5$
Pr, Pr$^n$: CH$_2$CH$_2$CH$_3$
Pr$^{iso}$: CH(CH$_3$)$_2$
Pr$^{cyclo}$: CH (CH$_2$)$_2$
Bu, Bu$^n$: CH$_2$CH$_2$CH$_2$CH$_3$
Bu$^{sec}$: CH(CH$_3$)C$_2$H$_5$
Bu$^{iso}$: CH$_2$CH(CH$_3$)$_2$
Bu$^{tert}$: C(CH$_3$)$_3$
Bu$^{cyclo}$: CH(CH$_2$)$_3$
Pn, Pn$^n$: CH$_2$CH$_2$CH$_2$CH$_2$CH$_3$
Pn$^{cyclo}$: CH(CH$_2$)$_4$
Pn$^{iso}$: CH$_2$CH$_2$CH(CH$_3$)
Pn$^{neo}$: CH$_2$C(CH$_3$)$_3$
Hex, Hex$^n$: CH$_2$(CH$_2$)$_4$CH$_3$
Hep, Hep$^n$: CH$_2$(CH$_2$)$_5$CH$_3$
Oct, Oct$^n$: CH$_2$(CH$_2$)$_6$CH$_3$
4-Cl—Ph: 4-Cl-Phenyl When the compound of the present invention is used as a herbicide or as a plant growth regulator, it is usually mixed with a suitable carrier, for instance, a solid carrier such as clay, talc, bentonite, urea, ammonium sulfate, walnut powder, diatomaceous earth or white carbon, or a liquid carrier such as water, an alcohol (such as isopropanol, butanol, ethylene glycol, benzyl alcohol or furfuryl alcohol), an aromatic hydrocarbon (such as toluene, xylene or methylnaphthalene), an ether (such as anisole), a vegetable oil (such as soybean oil or cottonseed oil), a ketone (such as cyclohexanone or isophorone), an ester (such as butyl acetate), an acid amide (such as N-methylpyrrolidone) or a hologenated hydrocabron (such as chlorobenzene). If desired, a surfactant, an emulsifier, a dispersing agent, a penetrating agent, a spreader, a thickner, a antifreezing agent, an anticaking agent, or a stabilizer may be added to prepare an optional formulation such as a liquid formulation, an emulsifiable concentrate, a wettable powder, a dry flowable, a flowable, a dust or a granule.

Further, the compound of the present invention may be combined with other herbicides, various insecticides, miticides, nematicides, fungicides, plant growth regulators, synergists, fertilizers or soil conditioning materials at the time of the preparation of the formulations or at the time of the application, as the case requires.

Particularly, combined use of the compound of the present invention with another agricultural chemical can be expected to result in lower cost attributable to reduction in the dose, a broader spectrum and a higher herbicidal or plant growth regulating effect attributable to synergistic action of the combined chemical. In such a case, the compound of the present invention can be combined with plural known agricultural chemicals simultaneously. The agricultural chemicals which may be used in combination with the compound of the present invention, may be, for example, compounds disclosed in Farm Chemicals Handbook (1994).

The dose of the compound of the present invention varies depending upon the application site, the season for application, the manner of application, weather conditions, the formulation, soil conditions, the type of crop plants and the like. However, it is usually within a range of from 0.000001 to 10 kg, preferably from 0.00001 to 5 kg per hectar (ha) as the amount of the active ingredient. However, when the compound of the present invention is used for promoting plant seed germination or initial growth, it is preferred to adjust the active ingredient concentration to a level of from 0.01 to 100 ppb before application.

Now, examples of formulations of the compounds of the present invention will be given. However, it should be understood that the present invention is by no means restricted to such specific examples. In the following Formulation Examples, "parts" means parts by weight.

| [Wettable powder] | |
|---|---|
| Compound of the present invention | 0.1–80 parts |
| Solid carrier | 10–90 parts |
| Surfactant | 1–10 parts |
| Other | 1–5 parts |

As the others, for example, an anticaking agent may be mentioned.

| [Emulsifiable Concentrate] | |
|---|---|
| Compound of the present invention | 0.1–30 parts |
| Liquid carrier | 30–95 parts |
| Surfactant | 5–15 parts |
| [Flowable] | |
| Compound of the present invention | 0.1–70 parts |
| Liquid carrier | 15–65 parts |
| Surfactant | 5–12 parts |
| Others | 5–30 parts |

As the others, for example, an antifreezing agent and a thickner may be mentioned.

| [Granular wettable powder (dry flowable)] | |
| --- | --- |
| Compound of the present invention | 0.1–90 parts |
| Solid carrier | 10–70 parts |
| Surfactant | 1–20 parts |
| [Granule] | |
| Compound of the present invention | 0.0001–10 parts |
| Solid carrier | 90–99.9999 parts |
| Others | 0.1–10 parts |
| [Liquid formulation] | |
| Compound of the present invention | 0.00001–30 parts |
| Liquid carrier | 0.1–50 parts |
| Water | 50–99.99 parts |
| Others | 0–10 parts |
| [Formulation for wiping] | |
| Compound of the present invention | 1–50 parts |
| Liquid carrier | 30–95 parts |
| Thickner | 5–50 parts |
| [Formulation for trunk injection] | |
| Compound of the present invention | 0.01–30 parts |
| Liquid carrier | 70–99.99 parts |
| [Formulation Example 1] Wettable powder | |
| Compound No. 5 of the present invention | 50 parts |
| Zeeklite PFP (tradename for a kaolin-type clay, manufactured by Zeeklite Industries, Co., Ltd.) | 43 parts |
| Sorpol 5050 (tradename for an anionic surfactant, manufactured by Toho Chemical Industry Co., Ltd.) | 2 parts |
| Lunox 1000C (tradename for an anionic surfactant, manufactured by Toho Chemical Industry Co., Ltd.) | 3 parts |
| Carplex #80 (anticaking agent) (tradename for a white carbon, manufactured by Shionogi Pharmaceutical Co., Ltd.) | 2 parts |

The above ingredients are homogeneously pulverized and mixed to form a wettable powder.

| [Formulation Example 2] Emulsifiable concentrate | |
| --- | --- |
| Compound No. 24 of the present invention | 3 parts |
| Xylene | 76 parts |
| Isophorone | 15 parts |
| Sorpol 3005X (tradename for a mixture of a nonionic surfactant and an anionic surfactant, manufactured by Toho Chemical Industry Co., Ltd.) | 6 parts |

The above ingredients are homogeneously mixed to form an emulsifiable concentrate.

| [Formulation Example 3] Flowable | |
| --- | --- |
| Compound No. 103 of the present invention | 35 parts |
| Agrizole S-711 (tradename for a nonionic surfactant, manufactured by Kao Corporation) | 8 parts |
| Lunox 1000C (tradename for an anionic surfactant, manufactured by Toho Chemical Industry Co., Ltd.) | 0.5 part |
| 1% Rodopol water (tradename for a thickner, manufactured by Rhone-Poulenc) | 20 parts |
| Ethylene glycol (antifreezing agent) | 8 parts |
| Water | 28.5 parts |

The above ingredients are homogeneously mixed to obtain a flowable.

| [Formulation Example 4] Granular wettable powder (dry flowable) | |
| --- | --- |
| Compound No. 111 of the present invention | 75 parts |
| Isoban No. 1 (tradename for an anionic surfactant, manufactured by Kuraray Isoprene Chemical Co., Ltd.) | 10 parts |
| Vanilex N (tradename for an anionic surfactant, manufactured by Sanyo-Kokusaku Pulp Co., Ltd.) | 5 parts |
| Carplex #80 (tradename; for a white carbon, manufactured by Shionogi Pharmaceutical Co., Ltd.) | 10 parts |

The above ingredients were homogeneously pulverized and mixed to form a dry flowable.

| [Formulation Example 5] Granule | |
| --- | --- |
| Compound No. 123 of the present invention | 0.1 part |
| Bentonite | 50.0 parts |
| Talc | 44.9 parts |
| Toxanone GR-31A (tradename for an anionic surfactant, manufactured by Sanyo Chemical Industries LTD.) | 5 parts |

The above ingredients are homogeneously mixed and pulverized, and after an addition of a small amount of water, the mixture was stirred, mixed and granulated by an extrusion-type granulating machine, followed by drying to obtain a granule.

| [Formulation Example 6] Liquid formulation | |
| --- | --- |
| Compound No. 101 of the present invention | 3 parts |
| 1-methoxy-2-propanol | 20 parts |
| Water | 77 parts |

The above ingredients are into a homogeneous solution to obtain a liquid formulation.

| [Formulation Example 7] Liguid formulation | |
| --- | --- |
| Compound No. 103 of the present invention | 0.0001 part |
| 1-methoxy-2-propanol | 1.0 part |
| Water | 98.9999 parts |

The above ingredients are mixed into a homogeneous solution to obtain a liquid formulation.

[Formulation Example 8] Formulation for wiping

| Compound No. 124 of the present invention | 10 parts |
| --- | --- |
| Thixogel VP (tradename, manufactured by Nissan Gardlar Shokubai K.K.) | 10 parts |
| Xylene | 80 parts |

[Formulation Example 9] Formulation for wiping

| Compound No. 119 of the present invention | 15 parts |
| --- | --- |
| Thixogel VP (tradename, manufactured by Nissan Gardlar Shokubai K.K.) | 10 parts |
| Highsol 100 (tradename, manufactured by Nisseki Chemical K.K.) | 75 parts |

-continued

[Formulation Example 10] Formulation for trunk injection

| | |
|---|---|
| Compound No. 114 of the present invention | 6 parts |
| Isopropanol | 94 parts |

[Formulation Example 11] Formulation for trunk injection

| | |
|---|---|
| Compound No. 106 of the present invention | 5 parts |
| Ethanol | 95 parts |

The above wettable powders, emulsifiable concentrates, flowables and granular wettable powders are diluted with water from 50 to 1,000 times before application, and are applied at a dose of from 0.000001 to 10 kg a hectar (ha) as the amount of the active ingredient.

Now, the usefulness of the compounds of the present invention as herbicides and plant growth regulators will be described in detail with reference to the following Test Examples.

[TEST EXAMPLE 1]

Test on the herbicidal effects in pre-emergence treatment on weeds under submerged conditions Wagner pots of 1/5000 a were filled with alluvial soil, and water was admixed to form a submerged state with a water depth of 4 cm. Seeds of barnyardgrass, bulrush, ducksalad and toothcup, and tubers of japanese ribbon wapato and perennial flat sedge were planted in the pots. Then, rice seedlings of 2 leaf stage were transplanted in the pots. The pots were placed in a greenhouse at a temperature of from 25° to 30° C., to culture the plants. A day after the planting, compounds of the present invention formulated in accordance with Formulation Examples were applied to the water surfaces at predetermined dose. Three weeks after the application, the herbicidal effects against various weeds and the influences on rice were determined on the basis of the 5-rank grading such that 0 means no effect, and 5 means complete death. The results are shown in Table 5-1. Each Compound No. in Table 5-1 corresponds to that in Examples, and the symbols in Table 5-1 have the following meanings.

A: barnyardgrass, B: bulrush, C: ducksalad, D: toothcup, E: japanese ribbon wapato, F: perennial flat sedge, a: rice

[TEST EXAMPLE 2]

Test on the herbicidal effects in post-emergence treatment on weeds under submerged conditions Wagner pots of 1/5000 a were filled with alluvial soil, and water was admixed to form a submerged state with a water depth of 4 cm.

In each of the above pots, seeds of barnyardgrass, bulrush, ducksalad and toothcup were sown, and the pots were placed in a greenhouse at a temperature of from 25° to 30° C. to culture the plants. 14 days after the seeding, the compound of the present invention formulated in accordance with Formulation Examples were applied to the water surfaces at predetermined doses. Three weeks after the application, the herbicidal effect against various weeds were determined on the basis of the 5-rank grading such that 0 indicates no effect, and 5 indicates complete death. The results are shown in Table 5-2. Each Compound No. in Table 5-2 corresponds to that in Examples, and the symbols in Table 5-2 have the following meanings.

A: barnyardgrass, B: bulrush, C: ducksalad, D: toothcup

[TEST EXAMPLE 3]

Test on the herbicidal effects in soil treatment

Plastic boxes having a length of 33 cm, a width of 33 cm and a depth of 8 cm were filled with diluvial soil, and seeds of barnyardgrass, green foxtail, wild oat, blackgrass, velvetleaf, common cocklebur, redroot pigweed, morningglory, persian speedwell, common chickweed, rice, corn, wheat, soybean, cotton and sugar beet were sown and covered with soil thereon in a thickness of about 1.5 cm, and then the compounds of the present invention formulated in accordance with Formulation Examples were applied onto the surfaces of the soil uniformly at predetermined doses. Three weeks after the application, the herbicidal effects against each weed and the influences on each crop plant were determined on the basis of the 5-rank grading such that 0 indicates no effect, and 5 indicates complete death. The results are shown in Table 5-3.

Each Compound No. in Table 5-3 corresponds to that in Examples, and the symbols in Table 5-3 have the following meanings.

G: barnyardgrass, H: green foxtail, I: wild oat, J: blackgrass, K: velvetleaf, L: common cocklebur, M: redroot pigweed, N: morningglory, 0: persian speedwell, P: common chickweed, a: rice, b: corn, c: wheat, d: soybean, e: cotton, f: sugar beet

[TEST EXAMPLE 4]

Test on the herbicidal effects in foliage treatment

A plastic boxes having a length of 33 cm, a width of 33 cm and a depth of 8 cm were filled with a sterilized diluvial soil, and seeds of barnyardgrass, green foxtail, wild oat, blackgrass, velvetleaf, common cocklebur, redroot pigweed, morningglory, persian speedwell, common chickweed, rice, corn, wheat, soybean, cotton and sugar beet were sown, and covered with soil in a thickness of about 1.5 cm. And the boxes were placed in a greenhouse at a temperature of from 25° to 30° C. for 14 days to culture the plants, and the compounds of the present invention formulated in accordance with Formulation Examples were applied to the foliages uniformly at predetermined doses. Three weeks after the application, the herbicidal effects against each weed and the influences on each crop plant were determined on the basis of the 5-rank grading such that 0 indicates no effect, and 5 indicated complete death. The results are shown in Table 5-4.

Each Compound No. in Table 5-4 corresponds to that in Examples, and the symbols in Table 5-4 have the following meanings.

G: barnyardgrass, H: green foxtail, I: wild oat, J: blackgrass, K: velvetleaf, L: common cocklebur, M: redroot pigweed, N: morningglory, 0: persian speedwell, P: common chickweed, a: rice, b: corn, c: wheat, d: soybean, e: cotton, f: sugar beet

[TEST EXAMPLE 5]

Test on the dwarfing effects in foliage treatment

Plastic pots having an inner diameter of 12 cm and a depth of 11 cm were filled with a sterilized diluvial soil, and seeds of rice, wheat, bermudagrass or bentgrass were sown in each pot, and were covered with the soil in a thickness of about 1 cm. The pots were placed in a green house at a temperature of from 25° to 30° C. to culture the plants. When each plant grew to the 1 or 2 leaf stage, the compounds of the present invention formulated in accordance with Formulation Examples were uniformly sprayed on the foliages at predetermined doses in terms of the active ingredients. Two weeks after the application, the dwarfing effects on each weed were determined by measuring the plant length and the plant age in leaf number. The results are shown in Table 5-5. Each Compound No. in Table 5-5 corresponds to that in Examples, and the symbols in Table 5-5 have the following meanings.

A: rice, B: wheat, C: bermudagrass, D: bentgrass

[TEST EXAMPLE 6]
Test on the dwarfing effects under submerged conditions

Plastic pots of 1/10000 a were filled with alluvial soil, and water was admixed to form a submerged state with a water depth of of 4 cm. Rice seedlings at about the 2 leaf stage having been raised in a nursery box were transplanted in the pots, and the pots were placed in a greenhouse at a temperature of from 25° to 30° C. to culture rice. When rice grew to about the 3.5 leaf stage, the compounds of the present invention formulated in accordance with Formulation Examples were applied to the water surfaces at predetermined doses. Two weeks after the application, the dwarfing effects on rice were determined by measuring the plant length and the plant age in leaf number. The results are shown in Table 5-6. Each Compound No. in Table 5-6 corresponds to that in Examples, and the symbols in Table 5-6 have the following meanings.

E: rice

[TEST EXAMPLE 7]
Test on the dwarfing effects in foliage treatment

Plastic pots having an inner diameter of 12 cm and a depth 11 cm were filled with a sterilized diluvial soil, and seeds of bermudagrass, bentgrass, soybean, cotton or wheat were sown in each pot, and were covered with the soil in a thickness of about 1 cm. The pots were placed in a greenhouse at a temperature of from 25° to 30° C. to culture the plants. When each plant grew to the 1 to 2 leaf stage, the foliages were sprayed so that the active ingredients would be applied at predetermined doses. The spray solutions were prepared by formulating the compounds of the present invention in accordance with Formulation Examples, and were sprayed onto the entire surfaces of the foliages of each plant by a small spray. Two weeks after the application, the dwarfing effects on each plant were determined by measuring the plant length and the plant age in leaf number. The results are shown in Table 5-7.

Each No. in Table 5-7 corresponds to the Compound No. in Examples, and the symbols in Table 5-7 have the following meanings.

A: bermudagrass, B: bentgrass, C: soybean, D: cotton, E: wheat

[TEST EXAMPLE 8]
Test on the dwarfing effects in foliage treatment

Plastic pots having an inner diameter of 12 cm and a depth of 11 cm were filled with a sterilized diluvial soil, and seeds of bermudagrass, bentgrass, soybean, cotton, wheat or rice were sown in each pot, and covered with the soil in a thickness of about 1 cm. The pots were placed in a greenhouse at a temperature of from 25 to 30° C. to culture the plants. When each plant grew to the 1 or 2 leaf stage, the foliages were uniformly sprayed so that the active ingredients would be applied at predetermined doses. The spray solutions were prepared by formulating the compounds of the present invention in accordance with Formulation Examples, and were applied onto the entire surfaces of the foliages of each plant by a small spray. Two weeks after the application, the dwarfing effects on each plant were determined by measuring the plant length and the plant age in leaf number. The results are shown in Table 5-8.

Each No. in Table 5-8 corresponds to the Compound No. in Examples, and the symbols in Table 5-8 have the following meanings.

A: bermudagrass, B: bentgrass, C: soybean, D: cotton, E: wheat, F: rice

TABLE 5-1

Test on the herbicidal effects in pre-emergence treatment on weeds under submerged conditions

| No. | Dose (g/a) | A | B | C | D | E | F | a |
|---|---|---|---|---|---|---|---|---|
| 2 | 20 | 5 | 3 | 0 | 2 | 0 | 0 | 1 |
| 4 | 20 | 2 | 5 | 5 | 5 | 4 | 0 | 0 |
| 5 | 20 | 5 | 4 | 4 | 5 | 0 | 0 | 0 |
| 6 | 20 | 5 | 3 | 5 | 5 | 0 | 0 | 0 |
| 7 | 20 | 4 | 1 | 1 | 5 | 2 | 2 | 0 |
| 8 | 8.3 | 2 | 3 | — | — | 3 | 2 | 0 |
| 9 | 20 | 2 | 3 | 3 | 5 | 2 | 0 | 0 |
| 10 | 20 | 4 | 1 | 1 | 5 | 1 | 2 | 2 |
| 11 | 14.8 | 4 | 0 | 1 | 5 | 0 | 0 | 2 |
| 12 | 10 | 3 | — | — | 3 | 2 | 2 | 0 |
| 13 | 10 | 4 | 2 | 3 | 5 | 1 | 3 | 2 |
| 14 | 10 | 1 | 2 | 3 | 5 | 0 | 0 | 0 |
| 16 | 10 | 0 | 0 | 0 | 2 | 0 | 0 | 0 |
| 17 | 10 | 0 | 0 | 2 | 2 | 0 | 0 | 0 |
| 18 | 10 | 0 | 0 | — | 2 | 0 | 2 | 0 |
| 19 | 10 | 0 | 0 | 0 | 2 | 0 | 0 | 0 |
| 20 | 10 | 5 | 5 | 5 | 5 | 0 | 3 | 0 |
| 21 | 10 | 5 | 5 | 5 | 5 | 0 | 2 | 0 |
| 22 | 10 | 5 | 5 | 5 | 5 | 0 | 0 | 2 |
| 23 | 10 | 5 | 5 | 5 | 5 | 0 | 3 | 0 |
| 24 | 10 | 5 | 5 | 5 | 5 | 4 | 3 | 1 |
| 101 | 20 | 5 | 0 | 0 | 2 | 0 | — | 1 |
| 102 | 6.4 | 0 | 0 | 0 | 0 | 0 | — | 0 |
| 103 | 10 | 5 | 5 | 5 | 5 | 5 | 5 | 2 |
| 104 | 20 | 1 | 1 | 1 | 5 | 0 | 5 | 0 |
| 105 | 20 | 5 | 5 | 5 | 5 | 0 | 5 | 0 |
| 106 | 20 | 5 | 5 | 5 | 5 | 5 | 5 | 3 |
| 107 | 20 | 1 | — | — | 5 | 2 | 2 | 0 |
| 108 | 20 | — | 4 | — | 5 | 3 | 4 | 0 |
| 109 | 20 | 2 | 4 | 0 | 5 | — | — | 0 |
| 110 | 5.9 | 5 | 2 | 2 | 5 | 0 | 3 | 2 |
| 111 | 10 | 5 | 5 | 5 | 5 | 4 | 5 | 3 |
| 112 | 10 | 5 | 3 | 4 | 5 | 3 | 5 | 3 |
| 113 | 20 | 2 | 2 | 2 | 5 | 1 | 3 | 0 |
| 114 | 10 | 5 | 5 | 5 | 5 | 5 | 5 | 2 |
| 115 | 10 | 2 | 2 | 2 | 2 | 0 | 0 | 0 |
| 116 | 10 | 4 | 5 | 5 | 5 | 0 | 3 | 0 |
| 117 | 10 | 3 | 3 | 4 | 5 | 0 | 0 | 0 |
| 118 | 10 | 5 | 5 | 5 | 5 | 0 | 5 | 0 |
| 119 | 10 | 5 | 5 | 5 | 5 | 2 | 3 | 0 |
| 120 | 10 | 0 | 2 | S | 8 | 2 | 0 | 0 |
| 121 | 10 | 5 | 5 | 5 | 5 | 0 | 2 | 0 |
| 122 | 10 | 4 | 2 | 5 | 5 | 0 | 0 | 2 |
| 123 | 10 | 5 | 5 | 5 | 5 | 5 | 3 | 1 |
| 124 | 10 | 5 | 5 | 5 | 5 | 3 | 5 | 0 |

TABLE 5-2

Test on the herbicidal effects in post-emergence treatment on weeds under submerged conditions

| No. | Dose (g/a) | A | B | G | D |
|---|---|---|---|---|---|
| 2 | 20 | 4 | 0 | 0 | 0 |
| 4 | 20 | 0 | 4 | 4 | 0 |
| 5 | 20 | 0 | 0 | 3 | 5 |
| 7 | 20 | 1 | 1 | 1 | 3 |
| 8 | 8.3 | 2 | — | — | 5 |
| 9 | 20 | 0 | 0 | 1 | 2 |
| 10 | 20 | 4 | 1 | 1 | 3 |
| 11 | 14.8 | 4 | 2 | 3 | 3 |
| 12 | 10 | 2 | — | — | — |
| 13 | 10 | 4 | 2 | — | 5 |
| 14 | 10 | 2 | 1 | 4 | 4 |
| 16 | 10 | 0 | 0 | 2 | 1 |
| 18 | 10 | 0 | 0 | 2 | 0 |
| 19 | 10 | 0 | 0 | 2 | 2 |
| 20 | 10 | 5 | 3 | 5 | 4 |
| 21 | 10 | 3 | 0 | 5 | 4 |
| 22 | 10 | 0 | 0 | 2 | 2 |
| 23 | 10 | 5 | 5 | 5 | 5 |

TABLE 5-2-continued

Test on the herbicidal effects in post-emergence treatment on weeds under submerged conditions

| No. | Dose (g/a) | A | B | G | D |
|---|---|---|---|---|---|
| 24 | 10 | 5 | 5 | 5 | 5 |
| 101 | 20 | 4 | 0 | 0 | 0 |
| 103 | 10 | 5 | 5 | 5 | 5 |
| 104 | 20 | 0 | 0 | 2 | 5 |
| 105 | 20 | 5 | 5 | 5 | 5 |
| 106 | 20 | 4 | 4 | 5 | 3 |
| 108 | 20 | 3 | 4 | 0 | 5 |
| 109 | 20 | 3 | 4 | 0 | 5 |
| 110 | 5.9 | 3 | 1 | 1 | 2 |
| 111 | 10 | 5 | 3 | 5 | 4 |
| 112 | 10 | 4 | 2 | 3 | 5 |
| 113 | 20 | 1 | 2 | 2 | 4 |
| 114 | 10 | 4 | 3 | 5 | 5 |
| 116 | 10 | 4 | 2 | 5 | 3 |
| 117 | 10 | 2 | 0 | 3 | 4 |
| 118 | 10 | 4 | 0 | 3 | 2 |
| 119 | 10 | 5 | 2 | 5 | 4 |
| 120 | 10 | 1 | 0 | 0 | 0 |
| 121 | 10 | 5 | 0 | 4 | 4 |
| 122 | 10 | 3 | 2 | 3 | 3 |
| 123 | 10 | 5 | 4 | 5 | 5 |
| 124 | 10 | 5 | 5 | 5 | 5 |

TABLE 5-3

Test on the herbicidal effects in soil treatment

| No. | Dose (g/a) | G | H | I | J | K | L | M | N | O | P | a | b | c | d | e | f |
|---|---|---|---|---|---|---|---|---|---|---|---|---|---|---|---|---|---|
| 2 | 50 | 3 | 2 | 3 | 2 | 4 | 3 | 2 | 4 | 5 | 5 | — | 2 | 0 | 2 | 0 | 1 |
| 3 | 50 | 0 | 0 | 0 | 0 | 1 | 4 | 5 | 2 | 4 | 5 | 0 | 0 | 0 | 0 | 0 | 1 |
| 5 | 50 | 0 | 0 | 0 | 0 | 0 | 0 | 5 | 0 | 5 | 5 | 0 | 0 | 0 | 0 | 0 | 0 |
| 6 | 50 | 0 | 0 | 0 | 0 | 2 | 0 | 5 | 0 | 0 | 0 | 0 | 0 | 0 | 0 | 0 | 0 |
| 7 | 50 | 8 | 0 | 0 | 3 | 5 | 3 | 5 | 3 | 5 | 5 | 1 | 0 | 0 | 2 | 0 | 4 |
| 8 | 20.8 | 0 | 0 | 0 | 0 | 2 | 0 | 5 | 0 | 3 | 3 | 0 | 0 | 0 | 0 | 0 | 0 |
| 9 | 50 | 0 | 0 | 2 | 0 | 4 | 4 | 5 | 0 | 4 | 3 | 0 | 0 | 0 | 0 | 0 | 1 |
| 10 | 50 | 5 | 4 | 0 | 0 | 5 | 4 | 5 | 4 | 5 | 5 | 2 | 1 | 0 | 1 | 2 | 3 |
| 11 | 37 | 5 | 4 | 3 | 3 | 4 | 4 | 5 | 4 | 5 | 5 | 3 | 2 | 0 | 0 | 0 | 1 |
| 13 | 25 | 0 | 1 | 0 | 0 | 1 | 0 | 5 | 2 | 4 | 4 | 0 | 0 | 0 | 0 | 0 | 0 |
| 14 | 25 | 0 | 0 | 0 | 0 | 0 | 0 | 4 | 0 | 0 | 3 | 0 | 0 | 0 | 0 | 0 | 1 |
| 16 | 25 | 0 | 0 | 0 | 2 | 0 | 0 | 5 | 0 | 5 | 4 | 0 | 0 | 0 | 0 | 0 | 2 |
| 18 | 25 | 0 | 0 | — | — | 0 | 0 | 4 | 0 | 0 | 3 | 0 | 0 | 0 | 0 | 0 | 0 |
| 19 | 25 | 0 | 0 | — | — | 0 | 0 | 5 | 0 | 2 | 3 | 0 | 0 | — | 0 | 0 | 0 |
| 20 | 25 | 5 | 4 | 0 | 2 | 0 | 0 | 5 | 0 | 5 | 5 | 0 | 0 | 0 | 0 | 0 | 2 |
| 21 | 25 | 0 | 0 | 0 | 0 | 0 | 0 | 5 | 0 | 5 | 5 | 0 | 0 | 0 | 0 | 0 | 0 |
| 22 | 25 | 4 | 3 | 3 | 3 | 2 | 4 | 5 | 4 | 5 | 5 | 2 | 1 | 0 | 0 | 1 | 2 |
| 23 | 25 | 0 | 0 | 0 | 0 | 0 | 0 | 5 | 2 | 5 | 5 | 0 | 0 | 0 | 0 | 1 | 3 |
| 24 | 25 | 5 | 4 | 3 | 5 | 0 | 3 | 5 | 3 | 5 | 5 | 1 | 0 | 2 | 0 | 0 | 5 |
| 101 | 50 | 5 | — | 4 | 4 | 5 | 4 | 5 | 4 | 5 | 5 | — | 2 | 1 | 3 | 2 | 2 |
| 102 | 16 | 0 | 0 | 0 | 0 | 0 | 0 | 2 | 0 | 0 | 0 | — | 0 | 0 | 0 | 0 | 0 |
| 103 | 25 | 5 | 5 | 5 | 4 | 5 | 4 | 5 | 5 | 5 | 5 | 5 | 4 | 3 | 4 | 4 | 4 |
| 104 | 50 | 4 | 5 | 0 | 0 | 4 | 0 | 5 | 0 | 5 | 3 | — | 0 | 0 | 1 | 0 | 0 |
| 105 | 50 | 5 | 5 | 0 | 5 | 3 | 2 | 5 | 5 | 5 | 5 | — | 0 | 4 | 0 | 0 | 1 |
| 106 | 50 | 5 | 5 | 5 | 5 | 5 | 5 | 5 | 4 | 5 | 5 | 5 | 3 | 3 | 5 | 3 | 4 |
| 108 | 50 | 5 | 4 | 3 | 0 | 5 | 3 | 5 | 2 | 5 | 4 | 0 | 0 | 0 | 3 | 1 | 0 |
| 109 | 50 | 0 | 0 | 0 | 0 | 2 | 0 | 4 | 0 | 5 | 2 | 0 | 0 | 0 | 0 | 0 | 0 |
| 110 | 15 | 5 | 5 | 2 | 2 | 5 | 4 | 5 | 3 | 5 | 5 | 3 | 1 | 0 | 0 | 1 | 1 |
| 111 | 25 | 5 | 5 | 2 | 5 | 5 | 4 | 5 | 3 | 5 | 5 | 2 | 1 | 0 | 2 | 0 | 3 |
| 112 | 25 | 5 | 4 | 3 | 5 | 4 | 5 | 5 | 4 | 5 | 5 | 2 | 1 | 1 | 2 | 1 | 3 |
| 114 | 25 | 5 | 5 | 0 | 4 | 5 | 5 | 5 | 5 | 5 | 5 | 4 | 3 | 0 | 4 | 3 | 4 |
| 116 | 25 | 5 | 5 | 4 | — | 0 | 0 | 4 | 0 | 4 | 4 | 2 | 0 | 0 | 0 | 0 | 2 |
| 117 | 25 | 0 | 0 | 0 | — | 0 | 0 | 5 | 0 | 4 | 3 | 0 | 0 | — | 0 | 0 | 0 |
| 118 | 25 | 4 | 0 | — | — | 0 | 0 | 4 | 0 | 2 | 0 | 0 | 0 | — | 0 | 0 | 0 |
| 119 | 25 | 5 | 5 | 0 | 0 | 4 | 4 | 5 | 5 | 5 | 5 | 1 | 0 | 0 | 0 | 0 | 4 |
| 121 | 25 | 0 | 0 | 0 | 0 | 0 | 0 | 5 | 0 | 5 | 5 | 0 | 0 | 0 | 0 | 0 | 1 |
| 122 | 25 | 5 | 3 | 0 | 4 | 4 | 2 | 5 | 3 | 5 | 5 | 2 | 0 | 0 | 1 | 0 | 1 |
| 123 | 25 | S | 5 | 3 | 5 | 5 | 5 | 5 | 4 | 5 | 5 | 3 | 3 | 3 | 3 | 3 | 5 |
| 124 | 25 | 5 | 5 | 3 | 5 | 5 | 5 | 5 | 5 | 5 | 5 | 5 | 3 | 3 | 3 | 4 | 4 |

TABLE 5-4

Test on the herbicidal effect in foliage treatment

| No. | Dose (g/a) | G | H | I | J | K | L | M | N | O | P | a | b | c | d | e | f |
|---|---|---|---|---|---|---|---|---|---|---|---|---|---|---|---|---|---|
| 2 | 50 | 2 | 1 | 2 | 1 | 0 | 1 | 0 | 3 | 1 | 3 | 1 | 1 | 0 | 0 | 0 | 0 |
| 3 | 50 | 0 | 0 | 0 | 0 | 0 | 0 | 0 | 0 | 0 | 1 | 0 | 0 | 0 | 0 | 0 | 0 |
| 5 | 50 | 0 | 0 | 0 | 0 | 0 | 0 | 2 | 0 | 0 | 0 | 0 | 0 | 0 | 0 | 0 | 0 |
| 7 | 50 | 3 | 0 | 0 | 0 | 1 | 1 | 1 | 2 | 2 | 2 | 0 | 0 | 0 | 0 | 0 | 0 |
| 8 | 21 | 0 | 0 | 0 | 2 | 0 | 0 | 0 | 0 | 3 | 4 | 0 | 0 | 0 | 0 | 0 | 0 |
| 9 | 50 | 3 | 0 | 4 | 3 | 1 | 0 | 5 | 0 | 2 | 5 | 0 | 0 | 0 | 0 | 0 | 1 |
| 10 | 50 | 0 | 3 | 0 | 1 | 3 | 3 | 2 | 2 | 2 | 4 | 0 | 0 | 1 | 0 | 0 | 0 |
| 11 | 37 | 4 | 4 | 1 | 4 | 3 | 3 | 4 | 5 | 3 | 4 | 1 | 1 | 0 | 1 | 0 | 0 |
| 12 | 25 | 1 | 0 | 0 | 0 | 2 | 0 | 1 | 0 | 0 | 0 | 0 | 0 | 0 | 0 | 0 | 0 |
| 13 | 25 | 1 | 1 | 0 | 0 | 1 | 0 | 3 | 0 | 0 | 2 | 0 | 0 | 0 | 0 | 0 | 0 |
| 14 | 25 | 0 | 0 | 0 | 0 | 0 | 4 | 0 | 0 | 3 | 0 | 0 | 0 | 0 | 0 | 0 | 1 |
| 16 | 25 | 0 | 0 | 0 | 3 | 3 | 0 | 0 | 0 | 4 | 3 | 0 | 0 | 0 | 0 | 0 | 0 |
| 19 | 25 | 0 | 0 | 0 | 0 | 0 | 0 | 2 | 0 | 0 | 0 | 0 | 0 | 0 | 0 | 0 | 0 |
| 22 | 25 | 0 | — | 2 | 2 | 0 | 0 | 0 | 0 | 0 | 3 | 0 | 0 | 0 | 0 | 0 | 0 |
| 24 | 25 | 1 | 1 | 3 | 4 | 0 | 2 | 0 | 0 | 5 | 5 | 0 | 0 | 0 | 0 | 0 | 2 |
| 101 | 50 | 3 | 2 | 3 | 4 | 3 | 2 | 2 | 3 | 3 | 4 | 1 | 2 | 1 | 2 | 1 | 1 |
| 102 | 16 | 0 | 0 | 0 | 0 | 0 | 1 | 0 | 0 | 1 | 0 | 0 | 0 | 0 | 0 | 0 | 0 |
| 103 | 25 | 5 | 4 | 3 | 5 | 2 | 5 | 3 | 3 | 4 | 4 | 1 | 2 | 1 | 3 | 1 | 2 |
| 104 | 50 | 9 | 2 | 0 | 0 | 3 | 3 | 2 | 1 | 3 | 1 | 0 | 0 | 0 | 0 | 0 | 0 |
| 105 | 50 | 5 | 5 | 0 | 5 | 3 | 3 | 5 | 3 | 5 | 5 | 3 | 0 | 0 | 1 | 1 | 4 |
| 106 | 50 | 4 | 3 | 5 | 5 | 4 | 5 | 3 | 5 | 5 | 4 | 4 | 1 | 3 | 3 | 0 | 5 |
| 108 | 50 | 3 | 3 | 3 | 4 | 2 | 0 | 2 | 0 | 4 | 4 | 0 | 0 | 1 | 0 | 0 | 1 |
| 109 | 50 | 3 | 2 | 0 | 0 | 0 | 0 | 3 | 2 | 3 | 4 | 0 | 0 | 0 | 0 | 0 | 0 |
| 110 | 15 | 3 | 5 | 2 | 3 | 3 | 1 | 3 | 3 | 3 | 4 | 1 | 1 | 1 | 0 | 0 | 0 |
| 111 | 25 | 4 | 4 | 3 | 3 | 3 | 3 | 3 | 4 | 3 | 3 | 1 | 1 | 1 | 2 | 1 | 0 |
| 112 | 25 | 4 | 4 | 3 | 3 | 3 | 2 | 3 | 4 | 3 | 3 | 1 | 1 | 1 | 1 | 1 | 0 |
| 114 | 25 | 4 | 5 | 4 | 4 | 4 | 5 | 4 | 5 | 4 | 4 | 1 | 2 | 0 | 3 | 1 | 2 |
| 116 | 25 | 4 | 3 | 0 | 3 | 3 | 5 | 3 | 5 | 5 | 3 | 0 | 0 | 1 | 0 | 1 |
| 117 | 25 | 0 | 0 | 0 | 2 | 0 | 0 | 0 | — | 5 | 0 | 0 | 0 | 0 | 0 | 0 | 0 |
| 118 | 25 | 5 | 0 | 0 | 4 | 4 | 0 | 4 | — | 3 | 0 | 1 | 0 | 0 | 0 | 0 | 0 |
| 119 | 25 | 5 | 8 | 0 | 4 | 3 | 2 | 4 | 3 | 5 | 5 | 4 | 1 | 2 | 2 | 1 | 3 |
| 121 | 25 | 0 | 0 | 0 | 0 | 0 | 0 | 0 | 0 | 4 | 4 | 0 | 0 | 0 | 0 | 0 | 2 |
| 122 | 25 | 2 | 2 | 0 | 3 | 0 | 2 | 2 | 4 | 0 | 3 | 1 | 0 | 2 | 0 | 0 | 0 |
| 123 | 25 | 3 | 3 | 3 | 4 | 3 | 2 | 2 | 1 | 5 | 5 | 2 | 2 | 1 | 1 | 0 | 2 |
| 124 | 25 | 5 | 4 | 2 | 4 | 3 | 3 | 3 | 2 | 5 | 5 | 3 | 3 | 1 | 2 | 1 | 2 |

TABLE 5-5

Test on the dwarfing effects in foliage treatment

| Compound No. | Dose (g/a) | Plant length (cm) | | | | Plant age in leaf number (Leaf stage) | | | |
|---|---|---|---|---|---|---|---|---|---|
| | | A | B | C | D | A | B | C | D |
| 1 | 0.1 | 37 | 29 | 15 | 15 | 5.5 | 4.6 | 5.5 | 3.5 |
| | 0.4 | 30 | 28 | 15 | 14 | 5.0 | 4.6 | 5.5 | 3.5 |
| | 1.6 | 30 | 26 | 15 | 10 | 5.0 | 4.6 | 5.5 | 3.5 |
| | 6.3 | 25 | 25 | 12 | 8 | 5.2 | 4.5 | 6.0 | 3.8 |
| | 25 | 17 | 23 | 8 | 5 | 5.5 | 4.6 | 6.0 | 3.8 |
| Non-treated area | — | 36 | 30 | 17 | 15 | 5.5 | 4.6 | 5.5 | 3.5 |

TABLE 5-6

Test on the dwarfing effects under submerged conditions

| Compound No. | Dose (g/a) | Plant length (cm) E | Plant age in leaf number (Leaf stage) E |
|---|---|---|---|
| 1 | 0.01 | 51 | 5.7 |
| | 0.1 | 51 | 5.8 |
| | 1 | 47 | 5.6 |
| | 10 | 37 | 5.5 |
| Non-treated area | — | 53 | 5.5 |

TABLE 5-7

Test on the dwarfing effects in foliage treatment

| No. | Dose (g/a) | Plant length (cm) | | | | | Plant age in leaf number (Leaf stage) | | | | |
|---|---|---|---|---|---|---|---|---|---|---|---|
| | | A | B | C | D | E | A | B | C | D | E |
| 101 | 1.6 | 14 | 4.5 | 41 | 22 | 24 | 5.5 | 3.5 | 4.5 | 2.1 | 5.0 |
| | 6.3 | 11 | 3 | 33 | 18 | 21 | 5.5 | 3.5 | 5.5 | 2.2 | 5.0 |
| | 25 | 3 | 1.5 | 22 | 13 | 20 | 5.5 | 3.5 | 4.0 | 2.0 | 4.8 |
| Non-treated area | — | 22 | 14 | 33 | 18 | 23 | 5.5 | 3.5 | 4.5 | 2.0 | 5.0 |

TABLE 5-8

Test on the dwarfing effects in foliage treatment

| Compound No. | Dose (g/a) | Plant length (cm) | | | | | | Plant age in leaf number (Leaf stage) | | | | | |
|---|---|---|---|---|---|---|---|---|---|---|---|---|---|
| | | A | B | C | D | E | F | A | B | C | D | E | F |
| 103 | 1.6 | 11 | 4 | 25 | 11 | 25 | 25 | 5.5 | 4.3 | 3.0 | 1.8 | 5.0 | 4.8 |
| | 6.3 | 6 | 3 | 15 | 9 | 22 | 20 | 5.3 | 2.5 | 3.0 | 1.2 | 5.0 | 4.5 |
| Non-treated area | — | 14 | 15 | 26 | 12 | 26 | 34 | 6.0 | 5.0 | 3.2 | 1.8 | 5.3 | 4.8 |

We claim:

1. A pyrimidine compound of the formula (1):

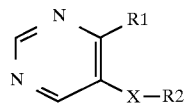

wherein:

R[1] is $C_1$–$C_6$ haloalkyl, $C_3$–$C_6$ cycloalkyl, $C_3$–$C_6$ cycloalkyl substituted by lower alkyl, $C_3$–$C_6$ halocycloalkyl or phenyl substituted by halogen, $C_1$–$C_4$ alkoxy, $C_1$–$C_3$ haloalkyl, $C_1$–$C_3$ haloalkoxy or phenyl;

R[2] is hydrogen, $C_1$–$C_6$ alkyl, $C_3$–$C_6$ cycloalkyl, $C_3$–$C_6$ cycloalkyl ($C_1$–$C_4$)alkyl, $C_1$–$C_6$ haloalkyl, $C_3$–$C_6$ halocycloalkyl, $C_3$–$C_8$ alkenyl, $C_3$–$C_8$ alkynyl, $C_1$–$C_2$ sulfonyl ($C_1$–$C_4$)alkyl, $C_4$ alkylthiol ($C_3$–$C_6$) cycloalkyl, phenyl or phenyl substituted by halogen, $C_1$–$C_4$ alkyl, $C_1$–$C_4$ alkoxy, $C_1$–$C_3$ haloalkyl, $C_1$–$C_3$ haloalkoxy or phenyl; and X is carbonyl or —C(R3)OH where R3 is hydrogen, $C_1$–$C_6$ alkyl, $C_3$–$C_8$ alkenyl, $C_3$–$C_8$ alkonyl, phenyl or phenyl substituted by halogen, $C_1$—$C_4$ alkyl, $C_1$–$C_4$ alkoxy, $C_1$–$C_3$ haloalkyl, $C_1$–$C_3$ haloalkoxy or phenyl;

with the proviso that when the carbon atom is an optically active carbon the racemic mixture and both the optical isomers thereof are included.

2. The pyrimidine compound of claim 1, which has one of the following formulae:

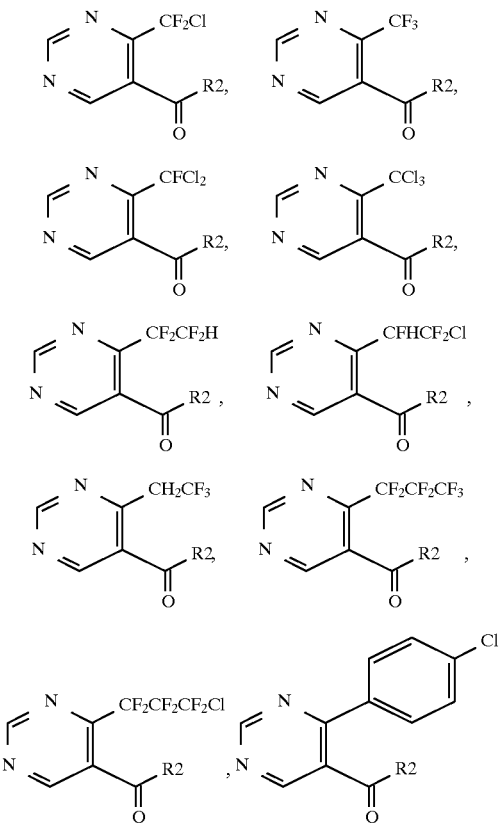

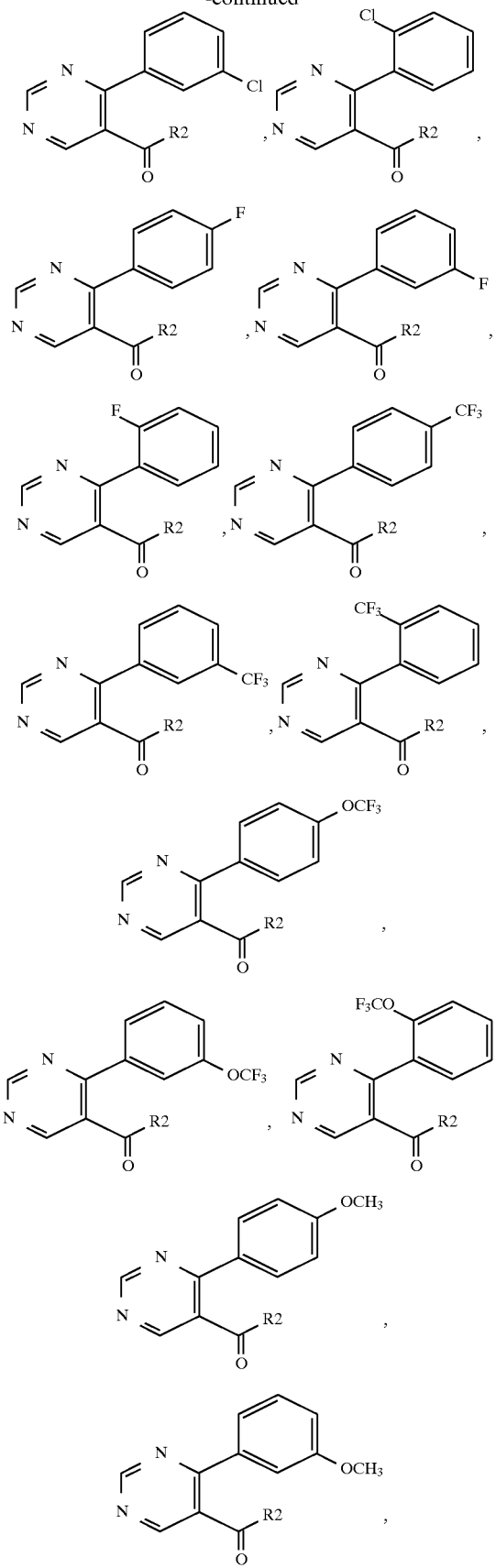

-continued

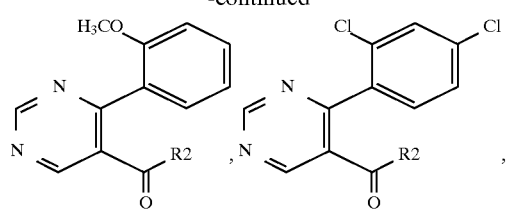

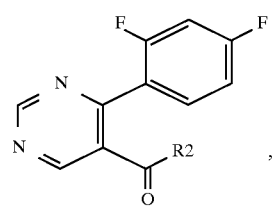

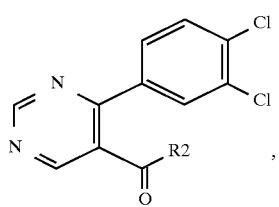

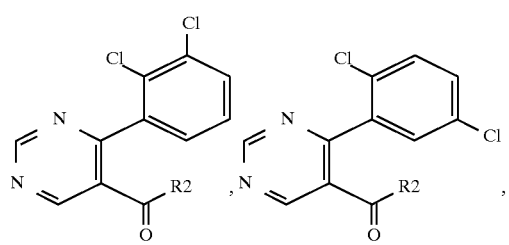

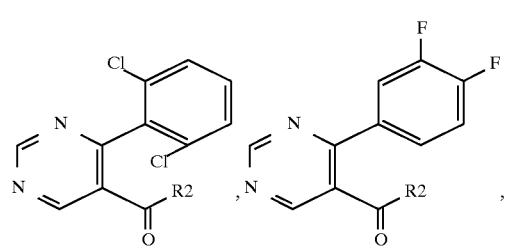

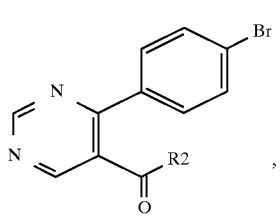

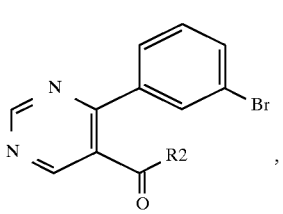

-continued

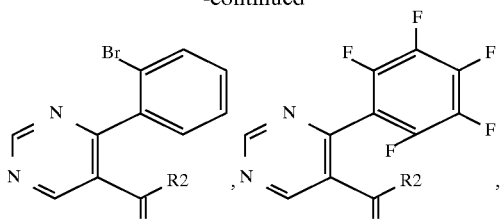

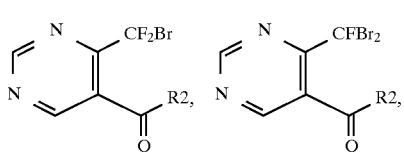

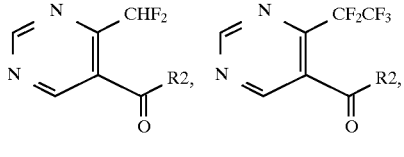

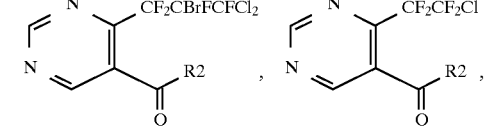

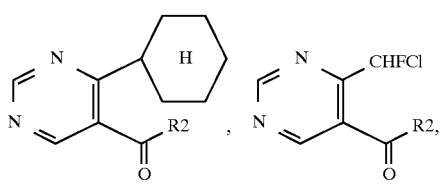

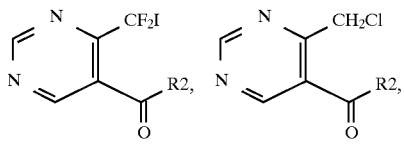

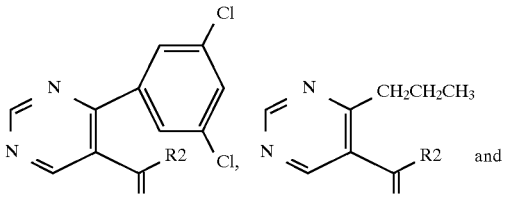 and

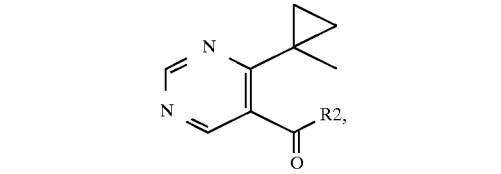

wherein R2 is selected from the group consisting of methyl, ethyl, propyl, isopropyl, cyclopropyl, butyl, sec-butyl, iso-butyl, tert-butyl, cyclobutyl, pentyl, neo-pentyl, iso-pentyl, cyclopentyl, hexyl, cyclohexyl, fluoromethyl, trifluoromethyl, trifluoroethyl, phenyl, 2-chlorophenyl, 3-chlorophenyl, 4-chlorophenyl, 2-fluorophenyl, 3-fluorophenyl, 4-fluorophenyl, 2-fluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2-trifluoromethoxyphenyl, 3-trifluoromethoxyphenyl, 4-trifluoromethoxyphenyl, 2-bromophenol, 3-bromophenol, 4-bromophenol, 2,4-dichlorophenyl, 3,4-dichlorophenyl, 2,6-dichlorophenyl, 2-fluoro-4-chlorophenyl, 2,4-difluorophenyl, 3,4-difluorophenyl, 2,5-dichlorophenyl, 2,3-dichlorophenyl, 2,6-difluorophenyl, bromomethyl, 3,5-dichlorophenyl, 2-methyl-4-chlorophenyl, 2-methyl-4-fluorophenyl, 1-methylsulfonylethyl, 1-methylcyclopropyl, 1-fluorocyclopropyl, 1-chlorocyclopropyl, 1-thiomethylcyclopropyl, 1-thioethylcyclopropyl, chloromethyl, $CF(Me)_2$, 1-cyclopropylethyl, $CH_2CH=CH_2$, $CH_2C\equiv CH$, $CH(Me)C\equiv CH$, $C(Me)_2C\equiv CH$, $CH(Me)CH=CH_2$, 2-tert-butylphenyl, 3-tert-butylphenyl, 4-tert-butylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-ethoxyphenyl, 2-isopropoxyphenyl and 2-propoxyphenyl.

3. The pyrimidine compound of claim 1, which has one of the following formulae:

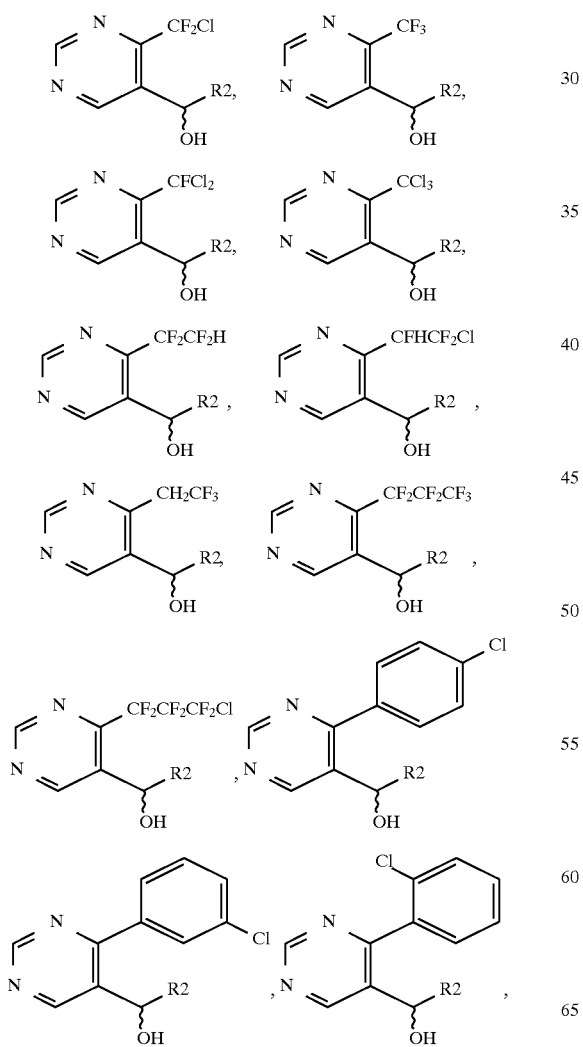

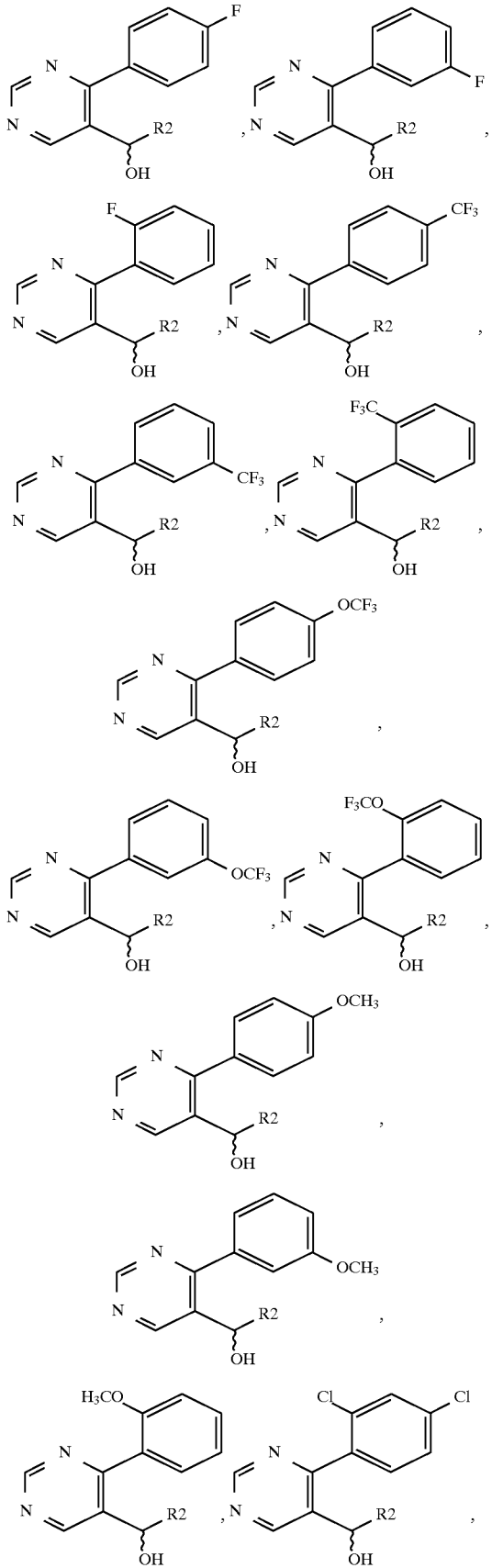

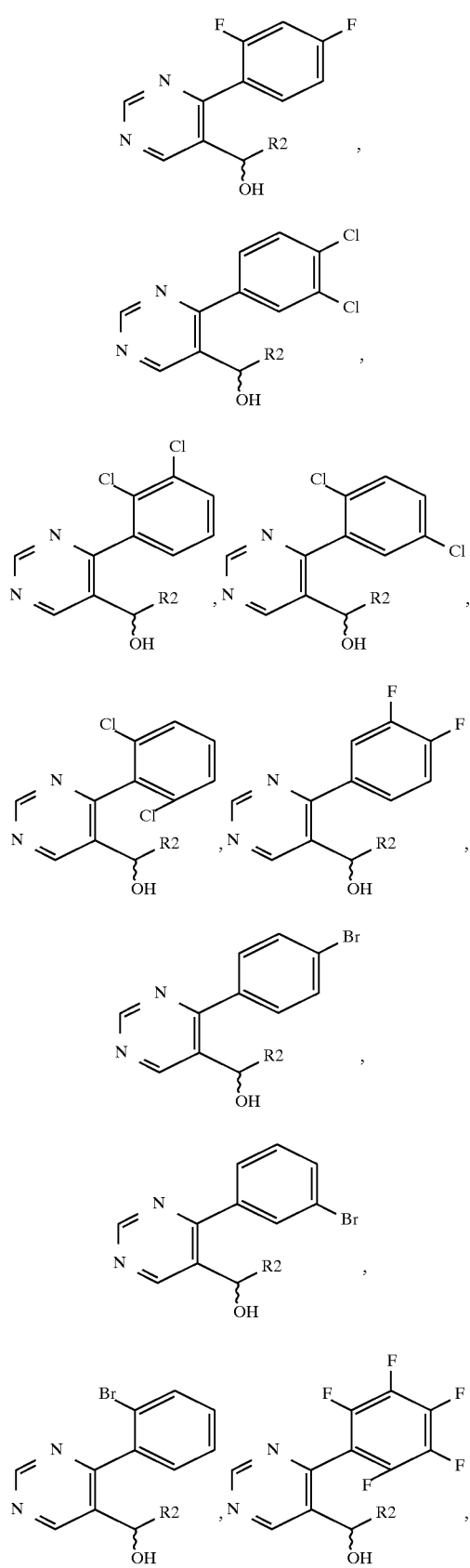

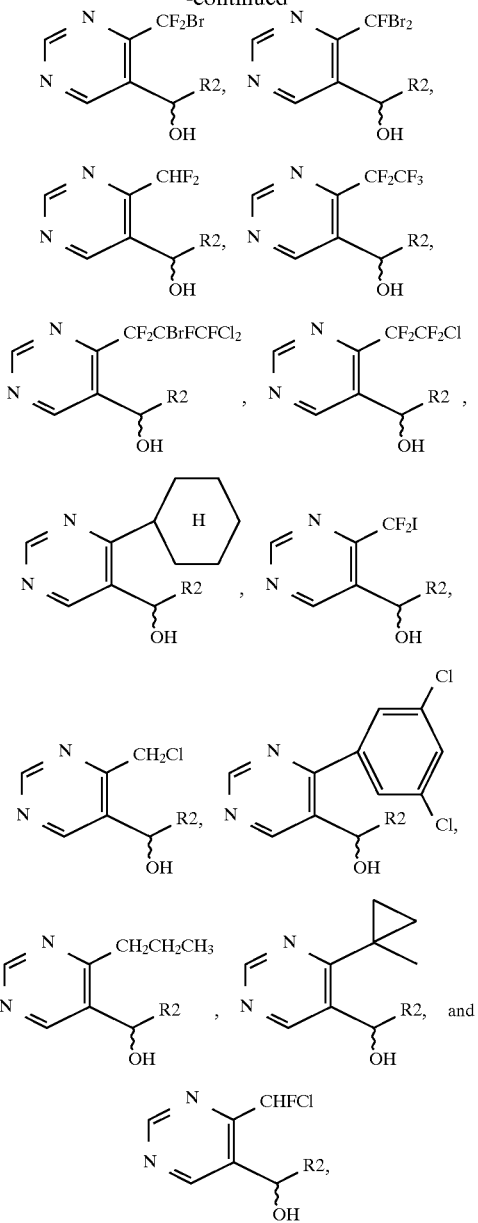

wherein R2 is selected from the group consisting of methyl, ethyl, propyl, isopropyl, cyclopropyl, butyl, sec-butyl, iso-butyl, tert-butyl, cyclobutyl, pentyl, neo-pentyl, iso-pentyl, cyclopentyl, hexyl, cyclohexyl, fluoromethyl, trifluoromethyl, trifluoroethyl, phenyl, 2-chlorophenyl, 3-chlorophenyl, 4-chlorophenyl, 2-fluorophenyl, 3-fluorophenyl, 4-fluorophenyl, 2-fluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2-trifluoromethoxyphenyl, 3-trifluoromethoxyphenyl, 4-trifluoromethoxyphenyl, 2-bromophenol, 3-bromophenol, 4-bromophenol, 2,4-dichlorophenyl, 3,4-dichlorophenyl, 2,6-dichlorophenyl, 2-fluoro-4-chlorophenyl, 2,4-difluorophenyl, 3,4-difluorophenyl, 2,5- dichlorophenyl, 2,3-dichlorophenyl, 2,6-difluorophenyl, bromomethyl, 3,5-dichlorophenyl, 2-methyl-4-chlorophenyl, 2-methyl-4-fluorophenyl, 1-methylsulfonylethyl, 1-methylcyclopropyl, 1-fluorocyclopropyl, 1-chlorocyclopropyl, 1-thiomethylcyclopropyl, 1-thioethylcyclopropyl, chloromethyl, $CF(Me)_2$, 1-cyclopropylethyl, $CH_2CH=CH_2$, $CH_2C\equiv CH$, $CH(Me)C\equiv CH$, $C(Me)_2C\equiv CH$, $CH(Me)CH=CH_2$, 2-tert-butylphenyl, 3-tert-butylphenyl, 4-tert-butylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-ethoxyphenyl, 2-isopropoxyphenyl and 2-propoxyphenyl.

4. The pyrimidine compound of claim 1, which has one of the following formulae:

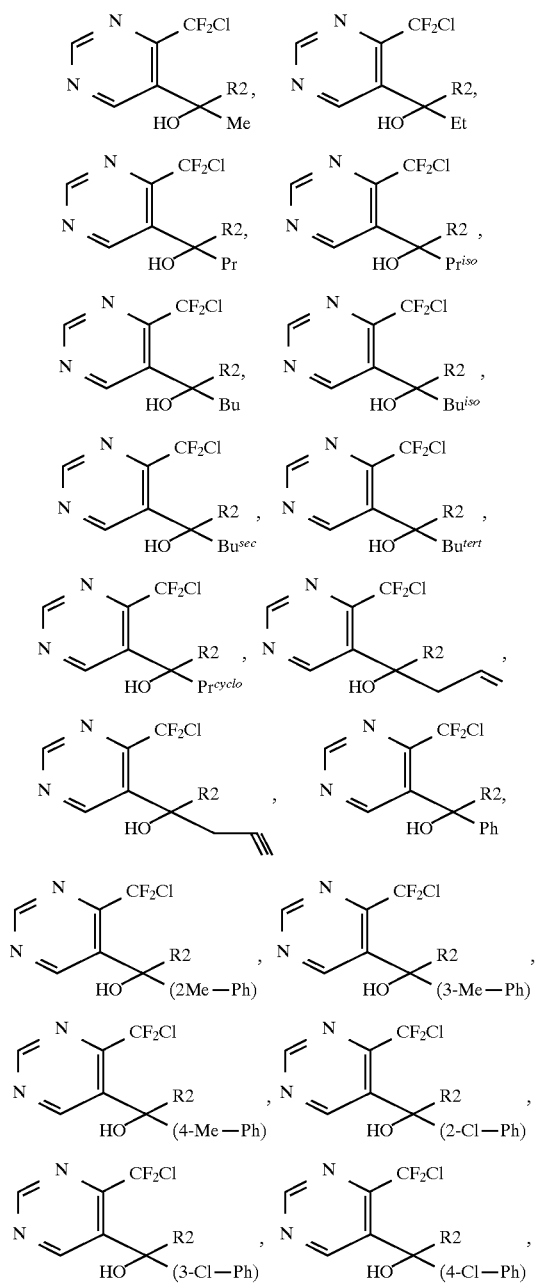

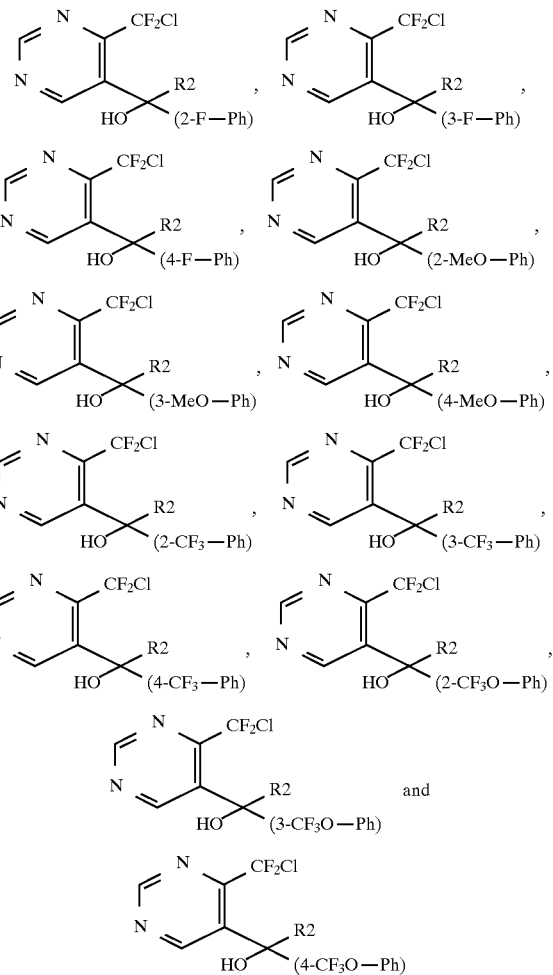

wherein R2 is selected from the group consisting of methyl, ethyl, propyl, isopropyl, cyclopropyl, butyl, sec-butyl, iso-butyl, tert-butyl, cyclobutyl, pentyl, neo-pentyl, iso-pentyl, cyclopentyl, hexyl, cyclohexyl, fluoromethyl, trifluoromethyl, trifluoroethyl, phenyl, 2-chlorophenyl, 3-chlorophenyl, 4-chlorophenyl, 2-fluorophenyl, 3-fluorophenyl, 4-fluorophenyl, 2-fluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2-trifluoromethoxyphenyl, 3-trifluoromethoxyphenyl, 4-trifluoromethoxyphenyl, 2-bromophenol, 3-bromophenol, 4-bromophenol, 2,4-dichlorophenyl, 3,4-dichlorophenyl, 2,6-dichlorophenyl, 2-fluoro-4-chlorophenyl, 2,4-difluorophenyl, 3,4-difluorophenyl, 2,5-dichlorophenyl, 2,3-dichlorophenyl, 2,6-difluorophenyl, bromomethyl, 3,5-dichlorophenyl, 2-methyl-4-chlorophenyl, 2-methyl-4-fluorophenyl, 1-methylsulfonylethyl, 1-methylcyclopropyl, 1-fluorocyclopropyl, 1-chlorocyclopropyl, 1-thiomethylcyclopropyl, 1-thioethylcyclopropyl, chloromethyl, $CF(Me)_2$, 1-cyclopropylethyl, $CH_2CH=CH_2$, $CH_2C\equiv CH$, $CH(Me)C\equiv CH$, $C(Me)_2C\equiv CH$, $CH(Me)CH=CH_2$, 2-tert-butylphenyl, 3-tert-butylphenyl, 4-tert-butylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-ethoxyphenyl, 2-isopropoxyphenyl and 2-propoxyphenyl.

5. A herbicidal composition, comprising:

a) one or more of the pyrimidine compounds of claim 1, and b) a suitable carrier.

6. A method of controlling weed growth, which comprises applying an effective amount of the pyrimidine compound of claim 1, on weeds or on soil containing weeds.

7. A method of controlling plant growth, which comprises applying an effective amount of the pyrimidine compound of claim 1, to a plant in need thereof or on soil containing the same.

8. The method of claim 7, wherein said plant growth control comprises inhibiting the growth of lawn grass.

9. The method of claim 7, wherein said plant growth control comprises controlling fruit tree turions.

10. The method of claim 7, wherein said plant growth control comprises dwarfing ornamental plants.

11. The method of claim 7, wherein said plant growth control comprises suppressing the growth of hedge plants.

12. The method of claim 7, wherein said plant growth control comprises controlling flowering of a plant.

* * * * *

UNITED STATES PATENT AND TRADEMARK OFFICE
CERTIFICATE OF CORRECTION

PATENT NO. : 5,773,388
DATED      : June 30, 1998
INVENTOR(S): Jun SATOW, et al.

It is certified that error appears in the above-identified patent and that said Letters Patent is hereby corrected as shown below:

On the title page, Item[87], the PCT Information, should read:

--[87]  PCT Pub. No.: WO/95/04725
        PCT Pub. Date: Feb. 16, 1995--

Signed and Sealed this

Thirtieth Day of March, 1999

Q. TODD DICKINSON

Attest:

Attesting Officer

Acting Commissioner of Patents and Trademarks